United States Patent
Brewer et al.

(10) Patent No.: US 10,293,101 B2
(45) Date of Patent: May 21, 2019

(54) DIABETES MANAGEMENT SYSTEM

(71) Applicant: Bigfoot Biomedical, Inc., Milpitas, CA (US)

(72) Inventors: Jeffrey Brewer, Palo Alto, CA (US); Kevin S. Lee, Milpitas, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 0 days.

(21) Appl. No.: 15/408,047

(22) Filed: Jan. 17, 2017

(65) Prior Publication Data

US 2017/0203030 A1 Jul. 20, 2017

Related U.S. Application Data

(60) Provisional application No. 62/278,977, filed on Jan. 14, 2016.

(51) Int. Cl.
*A61M 5/142* (2006.01)
*A61M 5/172* (2006.01)

(52) U.S. Cl.
CPC ....... *A61M 5/14244* (2013.01); *A61M 5/1723* (2013.01); *A61M 2005/14268* (2013.01); *A61M 2205/3303* (2013.01); *A61M 2205/3546* (2013.01); *A61M 2205/3553* (2013.01); *A61M 2205/3561* (2013.01); *A61M 2205/3569* (2013.01); *A61M 2205/3584* (2013.01); *A61M 2205/502* (2013.01); *A61M 2205/52* (2013.01); *A61M 2205/8206* (2013.01)

(58) Field of Classification Search
None
See application file for complete search history.

(56) References Cited

U.S. PATENT DOCUMENTS

| | | | |
|---|---|---|---|
| 7,591,801 B2 * | 9/2009 | Brauker | A61B 5/0002 604/161 |
| 7,776,031 B2 | 8/2010 | Hartlaub et al. | |
| 8,755,269 B2 | 6/2014 | Jollota | |
| 9,088,482 B2 * | 7/2015 | Shah | G06Q 10/06 |
| 2007/0060871 A1 | 3/2007 | Istoc et al. | |
| 2008/0058773 A1 | 3/2008 | John | |
| 2008/0199894 A1 | 8/2008 | Galasso | |

(Continued)

OTHER PUBLICATIONS

International Search Report and Written Opinion in Application No. PCT/US2017/013778, dated May 5, 2017, 13 pages.

(Continued)

*Primary Examiner* — John F Mortell
(74) *Attorney, Agent, or Firm* — Fish & Richardson P.C.

(57) ABSTRACT

A variety of location-based and/or proximity-based features related to diabetes management systems can be used to improve maintenance compliance and/or to provide important information to PWD designated assistance entities (e.g., family, friends, givers, HCPs, emergency medicine providers) under certain conditions. In some cases, a user's location can be tracked or determined to trigger and/or time alerts about upcoming maintenance tasks in a way that will increase the likelihood that the PWD will immediately perform the designated maintenance task. In some cases, methods, devices, and systems provided herein can use proximity to non-paired mobile computing devices to deliver data to PWD designated assistance entities.

11 Claims, 13 Drawing Sheets

(56) References Cited

U.S. PATENT DOCUMENTS

| | | | |
|---|---|---|---|
| 2011/0072422 A1 | 3/2011 | Brauer | |
| 2011/0092907 A1 | 4/2011 | Krogh et al. | |
| 2011/0124996 A1* | 5/2011 | Reinke | A61M 5/14248 |
| | | | 600/365 |
| 2013/0018677 A1* | 1/2013 | Chevrette | G06Q 40/08 |
| | | | 705/4 |
| 2016/0051749 A1 | 2/2016 | Istoc | |
| 2016/0379282 A1* | 12/2016 | Hill | G06Q 50/01 |
| | | | 705/26.1 |

OTHER PUBLICATIONS

International Preliminary Report on Patentability in Application No. PCT/US2017/013778, dated Jul. 26, 2018, 10 pages.

'google.github.io' [online]. "Walk up and use anything," Published on or before Oct. 3, 2014, Retrieved from the Internet: URL<https://google.github.io/physical-web/.>. 5 pages.

'developers.google.com' [online]. "Mark up the world using beacons," Published on or before Jul. 15, 2015, Retrieved from the Internet: URL<https://developers.google.com/beacons/>. 6 pages.

\* cited by examiner

| | |
|---|---|
| System Information Devices | |
| INSULIN PUMP - PUMP 1 | |
| Battery | 23.30% |
| Infusion Set | 2 Days to Change |
| Connection | Good |
| Insulin | 25.00% |
| CGM - 1NDNDN | |
| Battery | 82.50% |
| Sensor Age | 67 Days, 3 Hours |
| Connection | Good |

FIG. 3

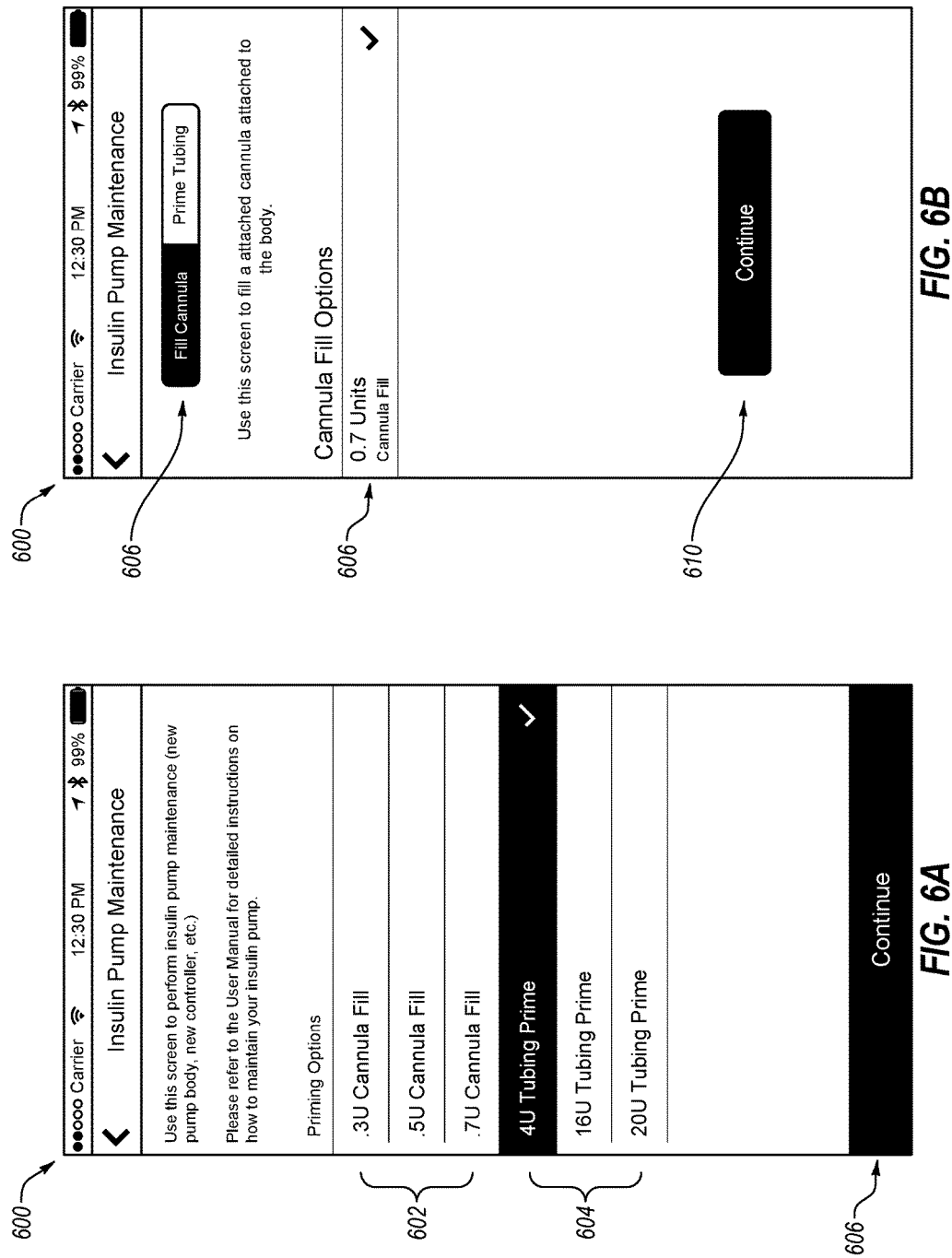

DIABETES MANAGEMENT SYSTEM

CROSS-REFERENCE TO RELATED APPLICATIONS

This application claims the benefit of U.S. Provisional Application Ser. No. 62/278,977, filed Jan. 14, 2016, and entitled "Location-Based Maintenance Reminders for Diabetes Management System," the entire contents of which are hereby incorporated by reference.

TECHNICAL FIELD

This document relates to using location and proximity to provide improved features as part of a diabetes management system.

BACKGROUND

Diabetes mellitus is a chronic metabolic disorder caused by an inability of a person's pancreas to produce sufficient amounts of the hormone, insulin, such that the person's metabolism is unable to provide for the proper absorption of sugar and starch. This failure leads to hyperglycemia, i.e. the presence of an excessive amount of analyte within the blood plasma. Persistent hyperglycemia has been associated with a variety of serious symptoms and life threatening long-term complications such as dehydration, ketoacidosis, diabetic coma, cardiovascular diseases, chronic renal failure, retinal damage and nerve damages with the risk of amputation of extremities. Because healing is not yet possible, a permanent therapy is necessary that provides constant glycemic control in order to constantly maintain the level of blood analyte within normal limits. Such glycemic control is achieved by regularly supplying external drugs to the body of the patient to thereby reduce the elevated levels of blood glucose.

Historically, diabetes is treated with multiple, daily injections of rapid and long acting insulin via a hypodermic syringe. One or two injections per day of a long acting insulin is administered to provide a basal level of insulin and additional injections of a rapidly acting insulin is administered before or with each meal in an amount proportional to the size of the meal. Insulin therapy can also be administered using an insulin pump that provides periodic or continuous release of the rapidly acting insulin to provide for a basal level of insulin and larger doses of that same insulin at the time of meals. Insulin pumps allow for the delivery of insulin in a manner that bears greater similarity to the naturally occurring physiological processes and can be controlled to follow standard or individually modified protocols to give the patient better glycemic control. In some circumstances, an insulin pump device can store (via input from a clinician or a user) a number of settings (e.g., dosage parameters or other settings) that are customized by the physician for the particular user.

People with diabetes (PWDs), their caregivers, and their health care providers (HCPs) bear a great deal of cognitive burden in managing diabetes. Delivering the correct amount of the medicine at the correct time is an extremely challenging endeavor, and an error that result in various conditions that can leave the PWD non-responsive. With the advent of the Nightscout Project (www.nightscout.info) and various commercial remote data monitoring solutions, PWDs have been able to share blood glucose data with caregivers, family, friends, etc., but these remote monitoring solutions each require the PWD to retain an operational smartphone that has internet connectivity and that is in close proximity to their CGM. Accordingly, there is a need for devices and systems that can alert caregivers and HCPs to potentially life-threatening situations even when the PWD's smartphone fails or lacks internet access.

Additionally, the use of an insulin pump and/or a CGM can require various routine and non-routine maintenance activities, which can interrupt the flow of daily life. Routine maintenance of a continuous glucose monitor can include calibrations and changing the sensor. If the PWD has an insulin pump, the PWD or their caregiver(s) must be ready to change our refill the insulin cartridge, recharge or replace the power source, change the infusion set, change the infusion site, etc. Constant alarms, alerts, and reminders for different conditions and maintenance tasks, however, can result in alarm fatigue, which can result in PWDs and the caregivers ignoring alarms to switching to less informative systems or forgetting to conduct routine maintenance tasks. Accordingly, there is a need to time alarms, alerts, and reminders to improve compliance with routine maintenance and reduce alarm fatigue.

SUMMARY

This document describes a variety of location-based and/or proximity-based features related to diabetes management systems. In some cases, a user's location can be tracked or determined to trigger and/or time alerts about upcoming maintenance tasks in a way that will increase the likelihood that the PWD will immediately perform the designated maintenance task. In some cases, a user's location can be determined and distributed to PWD designated assistance entities (e.g., family, friends, givers, HCPs, emergency medicine providers) under certain conditions, such a the detection of a potentially life-threatening situation. In some cases, methods, devices, and systems provided herein can use proximity to non-paired mobile computing devices to deliver data to PWD designated assistance entities, especially in cases where a paired mobile controlling device (e.g., the PWD's smartphone) is unavailable or fails or lacks an internet connection.

In a first set of implementations, methods, devices, and systems provided herein can improve user compliance with recommended maintenance activities by detecting locations where the user conducts maintenance activities and/or locations where the user is typically located for long periods of time, and determining when to provide a maintenance activity reminder based on the location of the user. In some of these implementations, methods, devices, and systems provided herein can ensure user privacy by encrypting location information and/or only storing location information on a mobile computing device.

According to example embodiment 1, a diabetes management system includes a mobile controller device and at least one of a continuous glucose monitor (CGM) or an insulin delivery device. In some cases example embodiment 1 can include both a CGM and an insulin delivery device. In some cases example embodiment 1 can have an insulin delivery device that determines a dosage of insulin based at least in part on glucose data from the CGM. The mobile controller device of example embodiment 1 can be adapted to (a) to receive blood glucose levels for a user from the continuous glucose monitor and/or (b) receive insulin delivery data from the insulin delivery device. The mobile controller device of example embodiment 1 is adapted to output maintenance reminders to the user based, at least in part, on location information. The mobile controller device of example embodiment 1 includes a location subsystem, a maintenance model, and a maintenance subsystem. The location subsystem of example embodiment 1 detects a location of the mobile controller device, the continuous glucose monitor, the insulin delivery device, or a combination thereof. The maintenance model of example embodiment 1 models the user's behavior with regard to maintenance reminders based, at least, on locations and context for the diabetes management system when the maintenance reminders are presented to the user. The maintenance subsystem of example embodiment 1 (i) continually updates the maintenance model by (a) detecting or receiving indications that the user has conducted maintenance tasks on the diabetes management system and (b) updating the maintenance model based on the conducted maintenance tasks, and (ii) continually provides maintenance reminders at optimal times for upcoming maintenance tasks by (a) obtaining a current location from the location subsystem, (b) determining a current context for the diabetes management system, and (c) identifying the optimal times and providing upcoming maintenance reminders for the upcoming maintenance tasks at the optimal times based on evaluation of the current context and the current location using the maintenance model.

According to example embodiment 2, a diabetes management system having the same features of example embodiment 1 can have the upcoming maintenance task be selected from the group consisting of recharging a continuous glucose monitor or an insulin delivery device, changing the sensor of a continuous glucose monitor, changing the infusion set of an insulin delivery device, changing the infusion location of an insulin delivery device, changing a sensor location for a continuous glucose monitor, refilling insulin into an insulin delivery device, changing an insulin containing cartridge in an insulin delivery device, replacing a battery in an insulin delivery device, or a combination thereof.

According to example embodiment 3, the diabetes management system of one of example embodiments 1 or 2 can include a mobile computing device adapted to connect to a Wi-Fi system and a location subsystem that detects the location of the mobile computing device based on available Wi-Fi systems at the location.

According to example embodiment 4, the diabetes management system of one of example embodiments 1 or 2 can include a mobile computing device that detects the location of the mobile computing device using a global positioning system (GPS).

According to example embodiment 5, the diabetes management system of one of example embodiments 1-4 can be configured such that the maintenance subsystem receives maintenance information from one or more of the insulin delivery device and the continuous glucose monitor about the conducted maintenance tasks and, in response to receiving the maintenance information, obtains (i) locations of the mobile controller device where the conducted maintenance tasks were performed and (ii) contexts of the diabetes management system when the conducted maintenance tasks were performed. The maintenance model of example embodiment 5 is updated based on combinations of (i) the conducted maintenance tasks, (ii) the locations where the conducted maintenance tasks were performed, and (iii) the contexts when the conducted maintenance tasks were performed.

According to example embodiment 6, the diabetes management system of example embodiment 5 can have the contexts of each of the conducted maintenance tasks were performed include, at least, a time of day when each of the conducted maintenance tasks were performed.

According to example embodiment 7, the diabetes management system of example embodiment 6 can have the contexts when each of the conducted maintenance tasks were performed further include, at least, a day of the week when each of the conducted maintenance tasks were performed.

According to example embodiment 8, the diabetes management system of one of example embodiments 1-7 can be configured such that for a particular upcoming maintenance task, the maintenance subsystem begins monitoring for an optimal time to provide a particular maintenance reminder for the particular upcoming maintenance task upon a determination that the particular upcoming maintenance task is due within a threshold first period of time, The monitoring in example embodiment 8 includes repeatedly obtaining the current location, determining the current context, and identifying the optimal time to provide the particular maintenance reminder. The monitoring for the particular upcoming maintenance task in example embodiment 8 is not performed before the particular upcoming maintenance task is due within the threshold first period of time.

According to example embodiment 9, the diabetes management system of example embodiment 8 can have the maintenance subsystem automatically provide the particular maintenance reminder regardless of the current location and the current context when the particular maintenance task is due within a threshold second period of time that is less than the first period of time.

According to example embodiment 10, the diabetes management system of one of example embodiments 1-9 can be configured such that the continual updating of the maintenance model includes the maintenance system (i) determining a particular location where the user conducts a majority of maintenance tasks, (ii) tracking the timing of a diurnal pattern of maintenance tasks at the particular location, and (iii) incorporating a diurnal period of time when the user is likely to conduct maintenance tasks representing the diurnal pattern of maintenance tasks into the maintenance model. Continually providing maintenance reminders in example embodiment 10 includes providing the maintenance reminders during the diurnal period of time prior to the scheduled time for the maintenance tasks when the user is at the particular location where the user conducts the majority of the maintenance tasks.

According to example embodiment 11, the diabetes management system of example embodiment 10 can be configured such that the maintenance reminders are held until the user arrives at the particular location where the user conducts the majority of maintenance tasks when the user is not at the particular location during the diurnal period of time when the user conducts most maintenance tasks.

According to example embodiment 12, the diabetes management system of example embodiment 11 can be configured such that the maintenance reminders are displayed at particular times when the maintenance tasks are scheduled regardless of whether the user is at the particular location where the user conducts a majority of maintenance tasks.

In a second set of implementations, methods, systems, and devices provided herein can allow peripheral devices related to diabetes management and insulin delivery, such as insulin pumps, other insulin delivery devices, sensors, monitoring systems, that have lost connectivity to a mobile controller device (e.g., the PWD's paired smartphone) to use other computing devices that are located nearby the peripheral device to communicate status information, alarms, and/or alerts to PWD designated assistance entities, either directly or via a remote computer system (e.g., cloud computer system). In some of these implementations, the computing devices can be authenticated as being used by a PWD designated assistance entity, which can permit a PWD designated assistance entity in close proximity (e.g., within BLUETOOTH range) to the peripheral device(s) to receive status information, alarms, and/or alerts for the PWD even without internet access. For example, such a feature can be helpful if the PWD and one or more PWD designated assistance entities travel to an area without internet access, and the paired mobile controlling device (e.g., the PWD's paired smartphone) becomes lost or disabled (e.g., out of battery). In some of these implementations, the computing device can be any computing device adapted to receive and relay messages in close proximity (e.g., within BLUETOOTH range) of the peripheral device(s) to a remote computer system (e.g., a cloud computer system), which can then send data (which can include location data) to one or more PWD designated assistance entities. For example, such a feature can be helpful if the PWD is unresponsive to a detected life-threatening alarm condition and the paired mobile controlling device is not available (e.g., experiencing communication issues, lost or far away, out of power) or failing to connect to the internet.

According to example embodiment 13, a wearable insulin delivery device can include an insulin pump device, one or more sensor interfaces, a wireless interface, a data storage device, an input subsystem, an output subsystem, and a controller. The insulin pump device is configured to administer insulin dosages to a patient wearing the insulin delivery device. The one or more sensor interfaces are adapted to obtain, at least, blood glucose levels for the patient. The wireless interface is configured to wirelessly communicate with one or more other computing. The data storage device stores a uniform resource locator (URL) for a remote server system and a unique identifier for the patient. The input subsystem receives input from the patient. The output subsystem outputs information to the patient. The controller is configured (i) to control the insulin pump device delivering insulin to the patient based, at least in part, on the blood glucose levels received through the one or more sensor interfaces, (ii) to securely communicate with a paired mobile computing device that is authorized to communicate with the remote server system regarding the patient, (iii) to automatically output an alarm via the output subsystem in response to an alarm condition, and (iv) to transmit a wireless beacon signal using the wireless interface in response to the patient failing to provide a response via the input subsystem within a threshold period of time of the alert being output. The beacon signal (i) includes, at least, the URL encoded with the unique identifier for the patient and (ii) is configured to prompt a third party computing device passively monitoring for beacon signals to transmit a request to the remote server system using the encoded URL.

In some cases, a computer in the remote server system of example embodiment 13 can analyze contextual information regarding a PWD to determine if an alarm is likely to represent an actual alarm condition. In some cases, the contextual information can include recent location data of the paired mobile computing device, recent blood glucose data for the PWD, and/or recent insulin delivery data for the PWD. In some cases, the alarm condition is a hypoglycemic event detected by a CGM. In some case, prior to transmitting the wireless beacon signal, one or more peripheral device issues an audible alarm of at least 45 decibels for at least 10 minutes without any user acknowledgement, which can be received via mobile computing device and/or one or more peripheral devices.

According to example embodiment 14, the insulin delivery device of example embodiment 13 is configured such that the wireless interface includes a BLUETOOTH wireless interface and the beacon signal is transmitted as a BLUETOOTH low energy (BLE) beacon signal with the encoded URL in a payload of the BLE beacon signal.

According to example embodiment 15, the insulin delivery device of one example embodiments 13 or 14 is configured such that the unique identifier for the patient is encoded in either a path of the URL or as a parameter appended to the URL and receipt of the encoded URL prompts the remote server system (i) to automatically determine one or more possible locations where the patient is currently located and (ii) to contact one or more of emergency personnel and authorized patient contacts as to the one or more possible locations where the patient is currently located. In some cases, example embodiment 15 can determine the one or more possible locations based at least in part on one or more locations of a location of the third party computing device. In some cases, example embodiment 15 can determine the one or more possible locations based at least in part on a last known location of the paired mobile computing device.

According to example embodiment 16, the insulin delivery device of one example embodiments 13-15 is configured such that the data storage device further stores health status information for the patient related to management of the patient's diabetes and the URL is further encoded with the health status information for the patient.

According to example embodiment 17, the insulin delivery device of one example embodiments 13-16 is configured such that the data storage device further location information for the patient communicated from the paired mobile computing device and the URL is further encoded with the location information for the patient.

According to example embodiment 18, a diabetes management system can include a paired mobile computing device, one or more other computing devices, an insulin delivery device, one or more sensors interfaces, a wireless interface, a data storage device, and a controller. The paired mobile computing device of example embodiment 18 is registered with a remote server system in association with a patient. The one or more other computing devices of example embodiment 18 are registered with the remote server system in association with one or more other patients. These one or more other computing devices are (i) preauthorized by the patient to receive and present health-related information for to the patient and (ii) to passively monitor for the health-related information transmitted over one or more local wireless protocols. The insulin delivery device of example embodiment 18 includes an insulin pump device to administer insulin dosages to the patient. The one or more sensor interfaces obtain, at least, blood glucose levels for the patient. The wireless interface of example embodiment 18 wirelessly communicates with the paired mobile computing device and the one or more other computing devices. The data storage device of example embodiment 18 stores (i) a unique identifier for the patient, (ii) authentication information to pair and securely communicate with the paired mobile computing device, and (iii) encryption information to securely broadcast the health-related information to the one or more other computing devices. The controller of example embodiment 18 is configured (i) to control the insulin pump device delivering insulin to the patient based, at least in part, on the blood glucose levels received through the one or more sensor interfaces, (ii) to securely communicate with the paired mobile computing device, and (iii) to broadcast secure wireless signals including the health-related information for detection and presentation by the one or more other computing devices in response to detecting no connectivity with the paired mobile computing device.

According to example embodiment 19, the diabetes management system of example embodiment 18 is configured such that the one or more other computing devices are each programmed (i) to request authentication from the patient before presenting the health-related information that has been transmitted by the insulin delivery device and detected by the one or more other computing devices, (ii) to receive input from the patient, (iii) to verify the input with the remote server system, and (iv) to output the health-related information in response to the input being verified with the remote server system.

According to example embodiment 20, the diabetes management system of one of example embodiments 18 or 19 is configured such that the wireless interface comprises a BLUETOOTH wireless interface and the broadcast secure wireless signals are transmitted as a BLUETOOTH low energy (BLE) beacon signal using one or more secure transmission protocols.

The details of one or more implementations of the invention are set forth in the accompanying drawings and the description below. Other features, objects, and advantages of the invention will be apparent from the description and drawings, and from the claims.

DESCRIPTION OF DRAWINGS

FIG. 3 is a user interface providing system status information.

FIGS. 6A-6D illustrate example screens for system maintenance.

Like reference symbols in the various drawings may indicate like elements.

DETAILED DESCRIPTION

Diabetes management systems provided herein can provide a user experience that improves routine maintenance compliance while avoiding alarm fatigue for a person with diabetes (PWD) and their caregivers. Diabetes management systems provided herein can also be adapted to provide alarms to PWD designated assistance entities (e.g., caregivers, loved ones, HPCs, and/or emergency medicine providers) if the PWD's mobile computing/controlling device fails. In some cases, a diabetes management system provided herein can include one or more of a mobile computing device (e.g., a smartphone), an insulin pump, a continuous glucose monitor, a blood glucose monitor, an insulin pen or syringe, and/or other components. Methods, devices, and systems provided herein can record when the user conducts a maintenance activity and record a user location for that activity. In some cases, methods, devices, and systems provided herein can upload location data, possibly in combination blood glucose data, insulin data, or other physiologically relevant data, to a remote server for distribution to one or more caregivers, HPCs, loved ones, emergency service providers, or any combination thereof. In some cases, methods, devices, and systems provided herein can broadcast secure wireless signals including the health-related information for detection and presentation by the one or more non-paired computing devices in response to detecting no connectivity with the paired mobile computing device (e.g., the paired smartphone).

Diabetes management systems and methods provided herein may be used and performed, respectively, by a user, for example, a type 1 or 2 diabetes patient or a caregiver of a diabetes patient. In some cases, the systems and methods may be adapted for use with additional chronic diseases or conditions, for example, unresponsive infections, cancer, cancer-related pain, chronic pain, gastrointestinal diseases or disorders, congestive heart failure, hemophilia, immune deficiencies, multiple sclerosis, and rheumatoid arthritis.

Diabetes Management System Overview

Figure 1A:
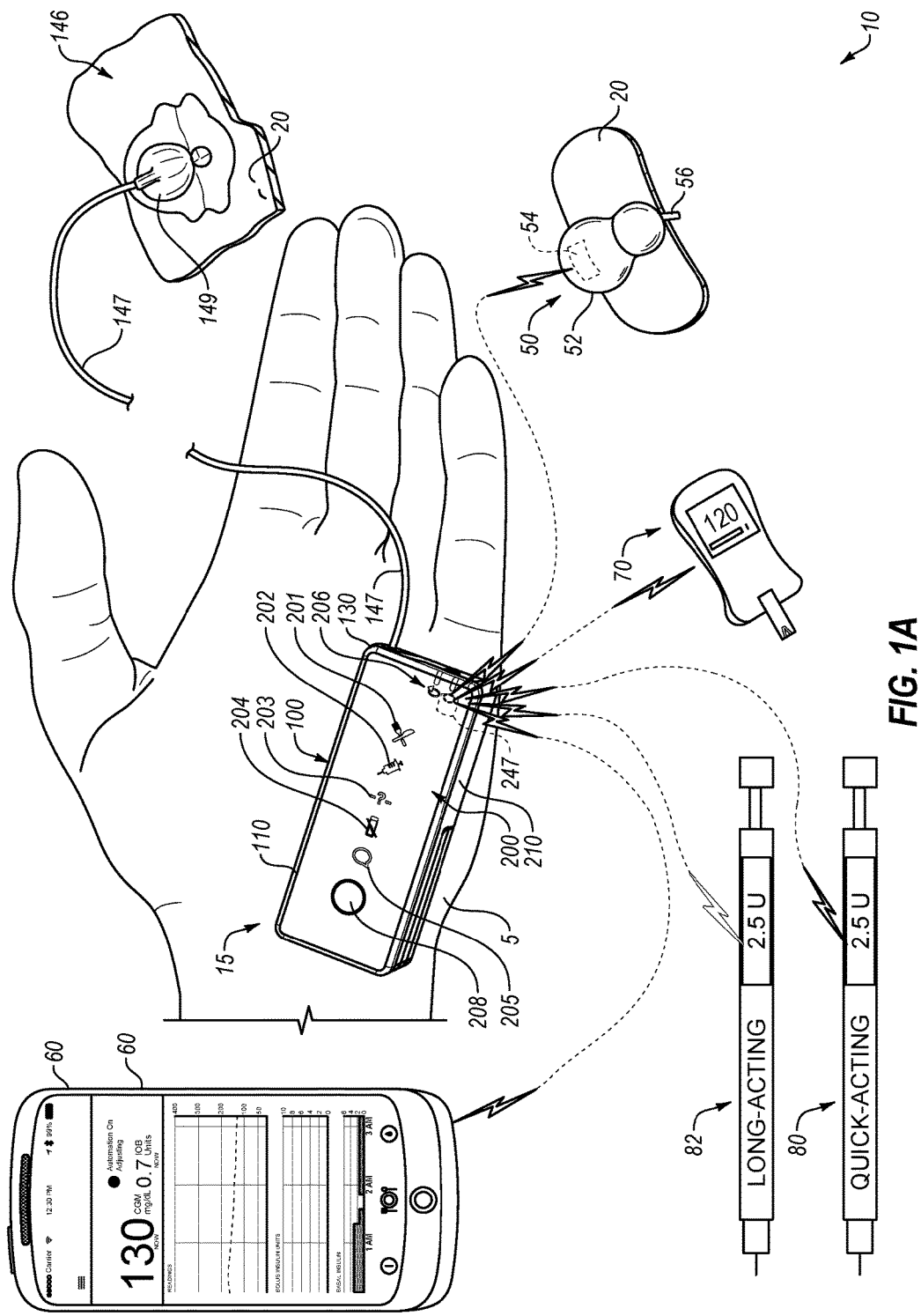
FIG. 1A is an exploded perspective view of an example diabetes management system.
Figure 1B:
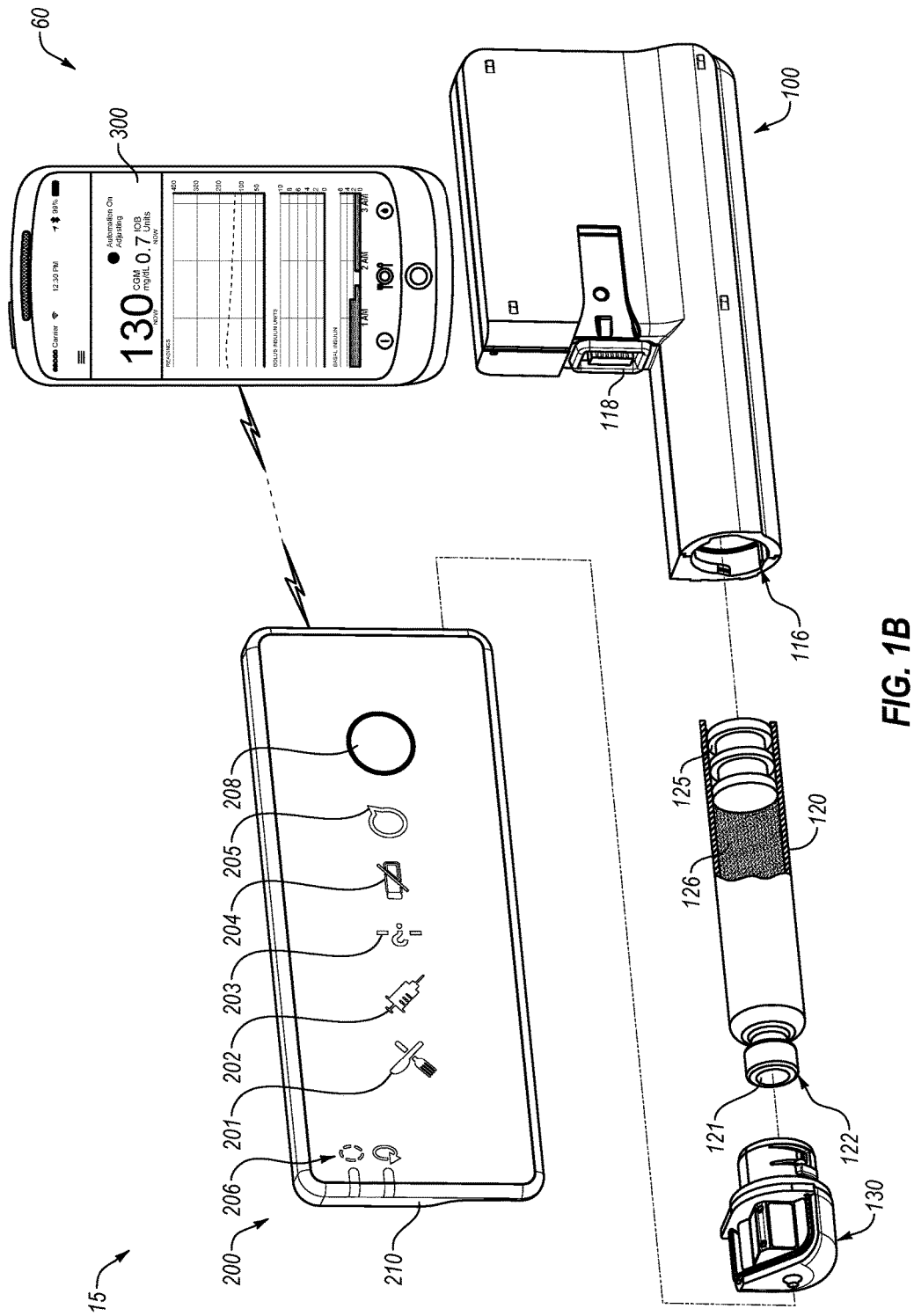
FIG. 1B depicts details about an exemplary insulin pump.
Figure 1C:
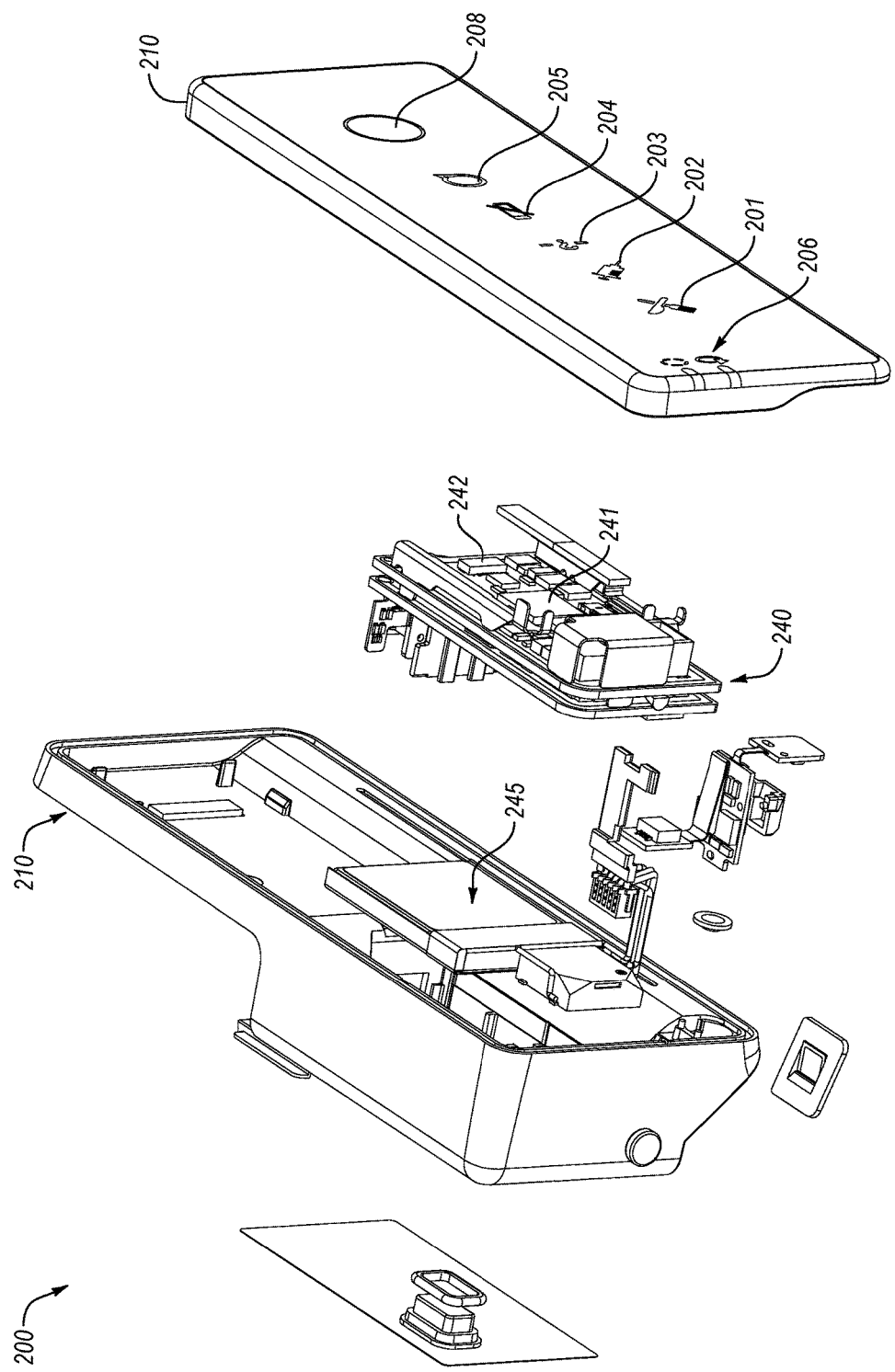
FIG. 1C depicts details about an exemplary insulin pump controller.

FIGS. 1A and 1B provide examples of a diabetes management system (DMS) 10 including an insulin pump assembly 15, a mobile computing device 60, a continuous glucose monitor 50, and a blood glucose monitor 70. FIG. 1C depicts the details of an exemplary pump controller, which can be used with DMS 10. Pump assembly 15 includes an infusion set 147 adapted to deliver insulin to an infusion site 146. In some cases, DMS 10 can include an insulin pen 80 or other insulin delivery device that can also be used to deliver insulin to a user. As shown, mobile computing device 60 is in wireless communication with insulin pump assembly 15. As shown, insulin pump assembly 15 is in wireless communication with continuous glucose monitor 50 and data from continuous glucose monitor 50 can be transferred to the mobile computing device 60 via insulin pump assembly 15. In some cases, continuous glucose monitor 50 can wirelessly communicate directly with mobile computing device 60. As shown, insulin pump assembly 15 is in wireless communication with blood glucose monitor 70 and data from blood glucose monitor 70 can be transferred to the mobile computing device 60 via insulin pump assembly 15. In some cases, blood glucose monitor 70 can wirelessly communicate directly with mobile computing device 60. In some cases, blood glucose monitor 70 can be unconnected from the system 10 and a user can manually input a blood glucose monitor reading into mobile computing device 60 (or into insulin pump assembly 15), either with or without a user prompt. In some cases, a blood glucose monitor 70 can be in wireless communication with the continuous glucose monitor 50.

As shown, controller 200 can include a limited user interface consisting of illuminable icons 201-206, which can provide indications regarding an operating mode of the pump assembly 15 and/or types of alarm or alert messages. In some cases, a user can view a more detailed message relating to an illuminated icon on the mobile computing device 60 via app 300. Controller 200 can additionally or alternatively issue audible notices (e.g., comprising audible words), audible tones, and/or haptic vibrations to indicate the presence of an alarm or alert. In some cases, alarm conditions can require more immediate user intervention, and can thus be presented with louder tones than alert conditions. In some cases, a button 208 can be present on controller 200 to permit user to check a status, using illuminable icons 201-206, and/or to snooze an alarm or alert. Although pump assembly 15 is depicted with a limited user interface intended to be used with a smartphone 60 and app 300 as the primary user interface, some implementations of the methods, devices, and systems provided herein can include a primary user interface directly on a pump assembly 15. In some cases, although depicted having a multi-part reusable/disposable construction, pump assemblies that are entirely disposable or entirely reusable and/or that have a unitary construction are also contemplated.

The features that are described herein can be extended to DMSs 10 that use alternative insulin delivery devices (e.g., insulin pens, patch pumps, syringes) and/or devices delivering other medicines (e.g., glucagon). In some cases, insulin pen 80 can be in wireless communication with mobile computing device 60. In some cases, user interfaces provided herein can be adapted to allow a user to manually input a bolus delivered using insulin pen 80. User interfaces described herein can also be used with any suitable insulin pump device, including patch pumps and/or other commercially available pumps. In some cases, an insulin pump assembly used in DSM 10 can have a unitary construction and have a reservoir adapted to be filled with insulin.

Exemplary Mobile Computing Device

Mobile computing device 60 can communicate with the controller device 200 through a wireless and/or wired connection with the controller device 200 (e.g., via a Bluetooth wireless communication connection in this particular implementations). In some cases, mobile computing device 60 communicates wirelessly with other elements of the system 10. Mobile computing device 60 can be any of a variety of appropriate computing devices, such as a smartphone, a tablet computing device, a wearable computing device, a smartwatch, a fitness tracker, a laptop computer, a desktop computer, and/or other appropriate computing devices able to detect a location of the mobile computing device. Sometimes location can be determined by detecting an available wifi network and/or other types of wireless networks/signals (e.g., detecting wireless beacon signals, BLUETOOTH signals, near field communication (NFC) signals). In some cases, location can be detected by using a global positioning system. In some cases, mobile computing device 60 can be used to transfer data from controller device 200 to the cloud. In some cases, the mobile computing device can be adapted to not share location information on the cloud or encrypt it so that it cannot be correlated to a physical address or latitude and longitude location. In some cases, the mobile computing device 60 provides a user interface (e.g., graphical user interface (GUI), speech-based user interface, motion-controlled user interface) through which users can provide information regarding maintenance activities and/or review upcoming scheduled maintenance tasks. Although mobile computing device 60 is depicted in FIG. 1 as including the primary user interface, with a limited user interface available on controller 200, in some cases methods, devices, and systems provided herein can have a primary user interface as part of pump assembly 15 and can operate with a mobile computing device 60 acting as a secondary user interface.

In implementations where the primary user interface is part of a mobile computing device, accessing the details of an alarm or an alert can require access to the paired mobile computing device. In some implementations of methods, systems, and devices provided herein, however, certain third-party devices can be authorized to allow connection to one or more peripheral devices of a diabetes management system (e.g., pump assembly 15, CGM 50, etc.) such that these authorized third-party devices (e.g., devices possessed by PWD designated assistance entities) can receive data from the peripheral devices, but not control the peripheral devices, even in the absence of an connected connected/operational paired mobile computing device. In some cases, the mobile computing device can be a mobile controlling device adapted to provide commands to the insulin pump assembly 15 (e.g., command the insulin pump assembly 15 to deliver a bolus).

User Interface

Figure 2:
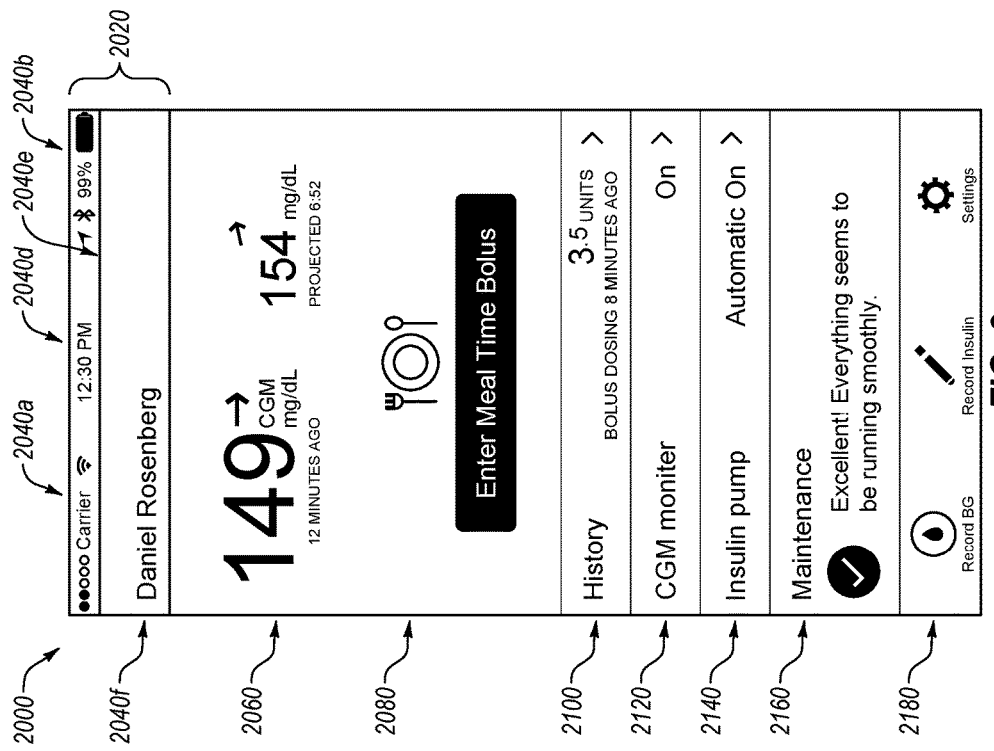
FIG. 2 is an example home screen of a mobile computing application for a diabetes management system.

FIG. 2 depicts an exemplary home screen 2000 for DMS 10, which can appear on a mobile computing device 60 when a user selects an icon for the DMS application. Home screen 200 is a user interface that can provide the user with a simplified view of the DMS status to help the user quickly understand whether the DMS system is operating appropriately and promote routine maintenance activities. As shown, homescreen 2000 includes a header 2020, which can include mobile and Wi-Fi signal strength indicators 2040a, a mobile computing device power display 2040b, a logo 2040c, a time display 2040d, and a user name 2040f.

Home screen 2000 includes a glucose measurement field 2060, a bolus entry user actionable display 2080, a history field 2100, a CGM monitor field 2120, an insulin pump field 2140, a maintenance field 2160 adapted to indicate to a user if the user will be expected to conduct any maintenance tasks in the near future (e.g., in the next 24 hours) and/or whether the DMS has detected any need for immediate maintenance, and an additional activities field 2180. Each of the fields 2060-2180 can include one or more selectable elements (e.g., buttons, arrows, selectable areas) that a user can select to view additional information and/or to provide input related to the field. Such selectable elements can be, for example, the entire field or a graphical subcomponent thereof.

The maintenance field 2160 can indicate, for example, when an infusion set is due for replacement, when an infusion site should be changed, when disposable parts of a pumping assembly need to be replaced and/or when an insulin reservoir needs to be refilled, when the continuous glucose monitor sensor needs to be changed or moved to a new location on the body, when a blood glucose measurement should be made to calibrate the continuous glucose monitor, or combinations thereof. In some cases, static indicators can indicate the approximate deadline for conducting routine maintenance, optionally with color indicators indicating the urgency of each maintenance task (e.g., red, yellow and green). In some cases, maintenance field 2160 can indicate that no maintenance tasks are required. In the cases that immediate maintenance is required (e.g., if the system is out of insulin), DMS 10 can provide an alarm (e.g., on the mobile computing device 60, pump assembly 15, or a combination thereof) to get the user to look at the user interface to learn about the required maintenance task, such as providing a push notification on the mobile computing device 60. In the cases that a maintenance task is less urgent (e.g., planned to be due in the next 12 hours or less, or within 10 hours, or within 8 hours, or within 6 hours, or within 4 hours, or within 3 hours, or within 2 hours, or within 1 hour), a maintenance alert can be triggered to get the user (e.g., the PWD) to acknowledge that a maintenance tasks is due shortly, with the exact timing of such alerts being based on the particular task. In some cases, methods, devices, and systems provided herein can time maintenance task alerts based on the location of the user.

Maintenance field 2160 is configured to reassure a user that system maintenance tasks are up-to-date, thus again reducing the cognitive burden on the user. Because the maintenance field 2160 is available for view at all times in the home screen 2000 (i.e., the maintenance field 2160 is persistently displayed on the home screen 2000), a user will not typically require frequent reminders about upcoming system maintenance.

Additionally, a user can view system status information, in a user interface, such as the example user interface 3000 shown in FIG. 3. As with the example home screen 2000, the user interface 3000 is presented on the mobile computing device 600. The example user interface 3000 depicts status information for components of the DMS 10 that are either directly or indirectly connected to the mobile computing device, such as the status information for the insulin pump assembly 15, the continuous glucose monitor 50, the blood glucose monitor 70, the infusion set 146, the external medication delivery devices 80, and/or other components of the DMS 10, including components that may be actively used and/or currently unused as part of the DMS 10. In the depicted example, the user interface 3000 depicts a first set of fields 3020 that provide status information for an insulin pump (e.g., insulin pump assembly 15) and a second set of fields 3040 for a CGM (e.g., CGM 50). This information includes, for example, remaining battery life, a time period until the component needs maintenance (e.g., number of days until the component needs to be changed), a status of the direct or indirect communication connection with the component (e.g., quality of a wireless or wired connection with the component), an age of the component (e.g., length over which the component has been used), a remaining supply of medicine or other consumable materials used by the components (e.g., remaining amount of insulin), and/or other information. The user interface 3000 can be presented, for example, in response to selection of the maintenance field 2160 when no actionable maintenance is requested of the user, which is the example status of the maintenance field 2160 depicted in FIG. 2.

Location Based Reminders

Figure 4A:
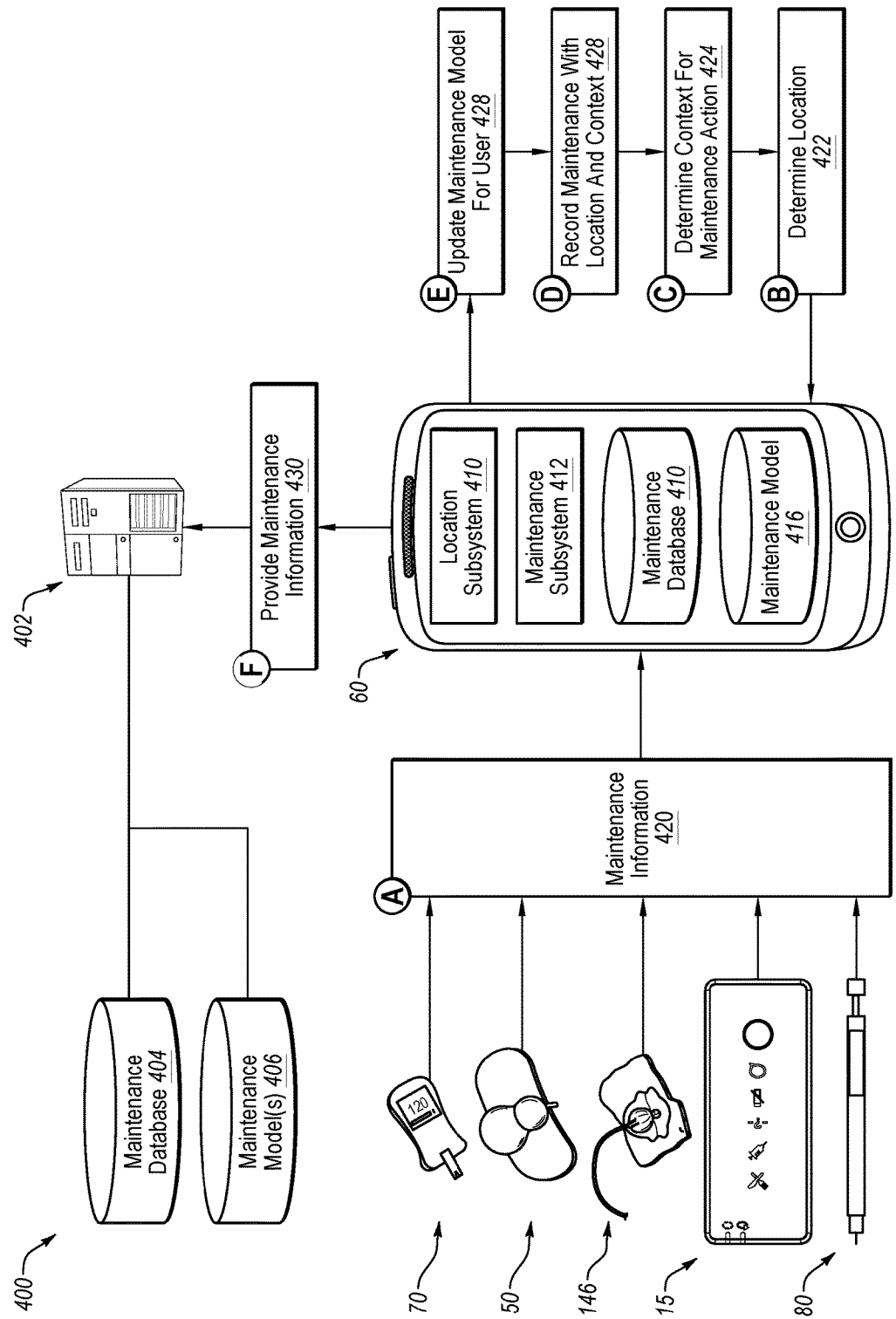
FIGS. 4A-B depict an example system for optimizing the delivery of maintenance reminders through the use of maintenance location tracking and other contextual information.
Figure 4B:
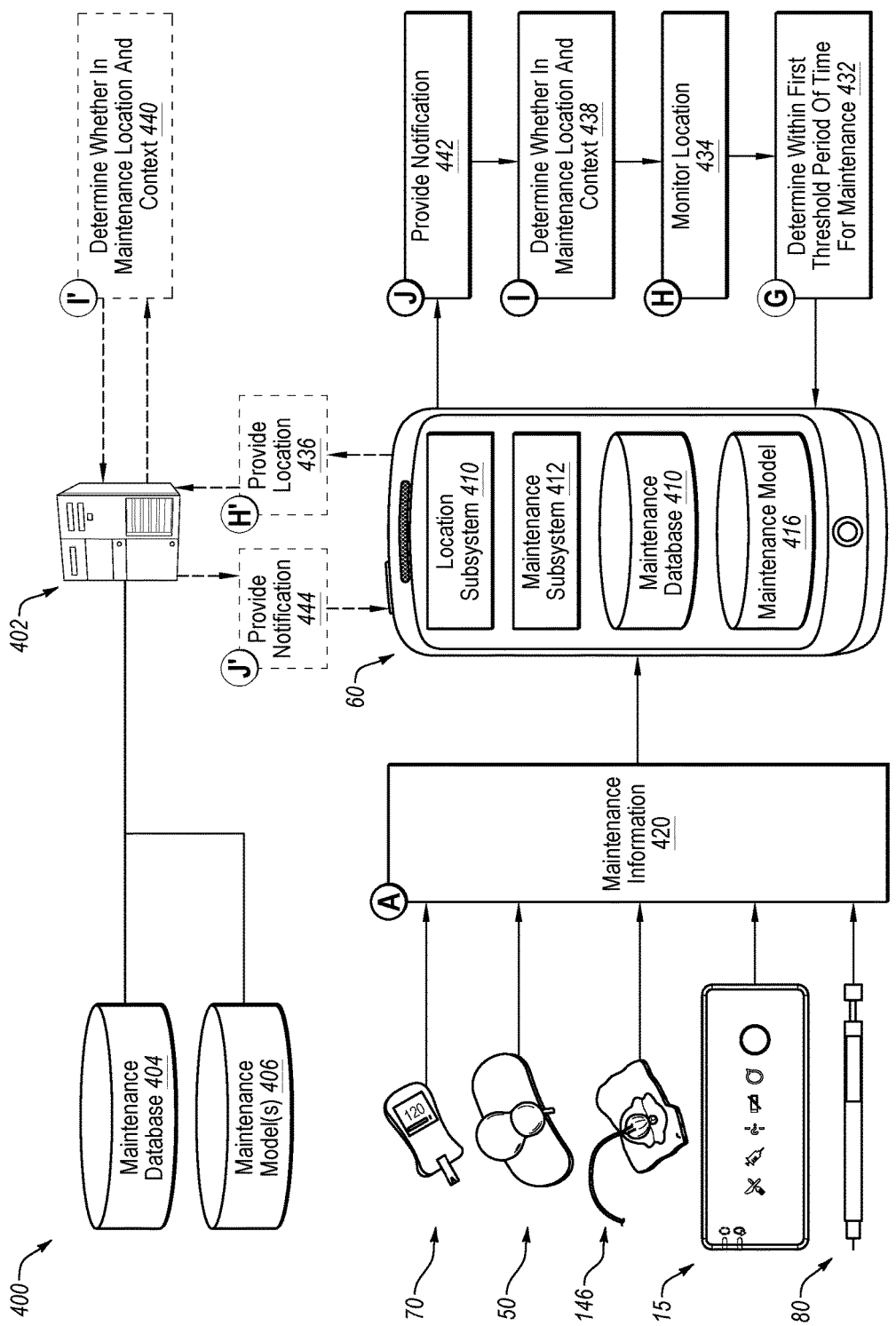

FIGS. 4A-B depict an example system 400 for optimizing the delivery of maintenance reminders through the use of maintenance location tracking and other contextual information. For example, the example system 400 is depicted as performing an example method that includes tracking where a user conducts routine maintenance tasks, the location of the user during the maintenance tasks, and a time of day when the maintenance task is completed (example contextual information), and providing reminders about upcoming maintenance activities based on the time of day (example contextual information) and the location of the user.

Referring to FIG. 4A, the example system 400 includes some or all of the components of the DMS 10, such as the mobile device 60, the insulin pump 15, the CGM 50, the BGM 70, the infusion set 146, and optionally the external medicine delivery device 80. The system 400 further includes a server system 402 (e.g., cloud computing system, web server system, application server system, frontend server system, backend server system, combinations thereof) that is specifically programmed to communicate with the mobile device 60 to administer the delivery of medicine to the user. The server system 402 is also specifically programmed to, in some case, monitor for and provide maintenance reminders for presentation on the mobile device 60. The server system 402 maintains a maintenance database 404 (e.g., cloud data storage system, secure data storage system, and/or combinations thereof) that log maintenance activities performed by the user along with corresponding location and contextual information (e.g., time of day, day of week, week of month, type of maintenance performed, component of the DMS 10 to which maintenance was performed, responsiveness to maintenance reminder, supply of materials when maintenance performed). The server system 402 also maintains maintenance models 406 (e.g., stored in cloud data storage system, secure data storage system, and/or combinations thereof) that model user behavior with regard maintenance activities.

The maintenance models 406 can be generated from the log of maintenance activities in the maintenance database 404 and can continually be refined as users perform maintenance activities and respond to maintenance reminders. Maintenance models 406 can be based any of a variety of user behavior data modeling techniques, such as artificial intelligence algorithms (e.g., neural networks, clustering algorithms, genetic algorithms, reinforcement learning, or combinations thereof) providing predictive assessments of future user behavior based on previous behavior and emerging user behavior patterns. Such maintenance models 406 can take a variety of details as inputs, such as the maintenance activity to be performed, the current time/day, the user's current location, the deadline to perform the maintenance activity, available supply of maintenance materials (e.g., insulin supply, replacement sensors), and/or other inputs, and can output an indication of whether the current time or a future time is an optimal one for providing a maintenance reminder to the user.

Still referring to FIG. 4A, the mobile device 60 includes a location subsystem 410 that determines a current location of the mobile device 60, which can be assumed to be the location of the user of the mobile computing device. The location of the user can additionally and/or alternatively be inferred as the location of other components of the DMS 10 that are able to detect a location. The location subsystem 410 can include one or more location modules, such as a global positioning system (GPS) module able to determine location from GPS satellite signals, a Wi-Fi positioning system programmed to correlate Wi-Fi base stations to a geographic location of the device 60, and/or other location positioning systems. The mobile computing device 60 further includes a maintenance subsystem 412 that is programmed to detect and log maintenance activities performed on the DMS 10, and to determine and provide maintenance reminders at optimal times. The maintenance subsystem 412 may operate alone or in combination with the server system 402 to provide maintenance features, such as detecting maintenance activities, logging maintenance activities, generating and updating maintenance models, determining when and what type of maintenance reminder to provide, and delivering maintenance reminders to users. For example, in some cases the maintenance subsystem 412 performs such maintenance features alone and without the server system 402. In other cases, the maintenance subsystem 412 identifies and provides maintenance data to the server system 402, which performs the maintenance reminder processing and provides maintenance reminders to the maintenance subsystem 412 to output on the mobile device 60. The mobile device 60 also includes a local maintenance database 414 (similar to the maintenance database 404) and a local maintenance model 416 (similar to the maintenance model 406) that the maintenance subsystem 412 can use to provide maintenance features.

Turning to the algorithm to provide maintenance reminders on the system 400, FIG. 4A depicts a sequence of steps A-F (420-430) for building a maintenance model for a user of the mobile device 60 and FIG. 4B depicts a sequence of steps G-J (432-444) for using the maintenance model to deliver maintenance reminders to the user at an optimal time. Referring to FIG. 4A, maintenance information for maintenance activities that are performed on the components of the DMS 10 is obtained by the mobile device 60, as indicated by step A (420). This information can be obtained directly or indirectly from these components by the mobile device 60, and can include information identifying, for example, recharging a continuous glucose monitor or an insulin delivery device, changing the sensor of a continuous glucose monitor, changing the infusion set of an insulin delivery device, changing the infusion location of an insulin delivery device, changing a sensor location for a continuous glucose monitor, refilling insulin into an insulin delivery device, changing an insulin containing cartridge in an insulin delivery device, replacing a battery in an insulin delivery device, or a combination thereof.

Once a maintenance activity has been identified, the mobile device 60 can determine the location of the user (step B, 422) and other contextual information (step C, 424) for the maintenance activity. The location can be determined, for example, using the location of the mobile device 60 as determined by the location subsystem 410. For instance, in some cases the location is detected by detecting a Wi-Fi network available. In some cases, the location is detected using a global positioning system (GPS). The contextual information can include, for example, the current time and date, the day of the week, the week of the year, the type of maintenance activity that is being performed, an existing supply of maintenance materials (e.g., extra insulin, replacement sensors), and/or other relevant contextual information related to settings and/or conditions that prompted the user to perform the maintenance. The maintenance can be recorded with the location and contextual information (step D, 426) and can be used to generate and/or update the maintenance model for the user (step E, 428), such as being recorded in the maintenance database 414 and updating the model 416. Additionally, the mobile device 60 can provide the maintenance information to the server system 402 (step F, 430), which can store the maintenance information in the database 404 and can use the maintenance information to generate/update the maintenance model 406 for the user. The maintenance model may be generated/updated by the mobile device 60, the server system 402, or combinations thereof. The server system 402 and the mobile device 60 may store redundant copies of the maintenance information and the maintenance model, and may sync data with each other when processing capacity and network bandwidth permit (e.g., during low bandwidth periods of time, like the middle of the night). The steps A-F (420-430) can be repeatedly and continually performed, and can be performed concurrently with the delivery of maintenance reminders via steps G-J (432-444).

Referring to FIG. 4B, the mobile device 60 can determine that the user is within a first threshold period of time of a maintenance deadline, as indicated by step G (432). The first threshold period of time can be, for example, a period within which maintenance is warranted but within which there is little to no health risk to the user if the maintenance is not immediately performed. For example, the first threshold period of time can be one day before the maintenance needs to be performed. Other timeframes can additionally or alternatively be used for the first threshold period of time. The first threshold period of time can vary depending on the type of maintenance being performed, the maintenance model for the user, and/or other factors. The maintenance activities and corresponding deadlines that are being monitored for can include, for example, recharging a continuous glucose monitor or an insulin delivery device, changing the sensor of a continuous glucose monitor, changing the infusion set of an insulin delivery device, changing the infusion set or infusion site of an insulin delivery device, changing a sensor location for a continuous glucose monitor, refilling insulin into an insulin delivery device, changing an insulin containing cartridge in an insulin delivery device, replacing a battery in an insulin delivery device, or a combination thereof.

In response to determining that the user has entered the first threshold period of time for a maintenance activity, the mobile device 60 can begin actively monitoring the user's location (step H, 434), similar to the location determinations described above with regard to step B (422). By delaying active location monitoring until the user is within the first threshold period of time of a maintenance activity deadline, the performance of the mobile device 60 in aggregate (during and outside of the first periods of time) can be improved. For example, location determination tasks performed by a mobile computing device can be resource intensive—meaning that they can consume a large amount of processor cycles, battery life, memory, network traffic, internal bus use, and/or other computing resources. Continually obtaining the location of the device 60 can be a drain on resources and can hamper performance of the device 60. Accordingly, the device 60 can be programmed to only determine its location during periods when its location is relevant to maintenance activities, such as when a maintenance activity is performed (step B, 422) and when the user is within the first threshold period of time of a maintenance activity deadline (step H, 434). By doing this, the performance of the device 60 can be increased without decreasing the quality of maintenance reminder-related services that are provided on device 60. Additionally, by polling for location information at limited times, the user privacy via the device 60 can be maximized while still providing the same quality of maintenance reminder-related services.

Location information and current context information for the device 60 can be obtained and fed into a maintenance model for the user to determine whether the user is currently in an optimal location and context to receive a maintenance reminder (step I, 438). For instance, in a simplified example, the model may indicate that the user is likely to perform a particular maintenance activity when the user is at his/her home on weekdays from 6-8 pm or on weekends from 10 am-noon. Such times and locations can, for example, be times and locations where the user has previously conducted that maintenance activity. The location information and context for the user can be repeatedly and continually fed into the maintenance model for the user to get a determination as to whether the user is currently at an optimal location and within an optimal context to receive a maintenance reminder. In response to receiving an indication that the current location and context are appropriate for a maintenance reminder, the mobile device can provide a maintenance reminder notification on the device (step J, 442). For example, a notification can be surfaced on the device 60 identifying the type of maintenance to be performed and the timeframe to perform the maintenance. Additionally and/or alternatively, the server system 403 can perform the steps H-J, as indicated by steps H'-J' (436, 440, 444). Example notifications that can be presented to a user are depicted in FIGS. 5-6.

In some cases, the system 400 (via the device 60 and/or the server system 402) can produce a maintenance reminder regardless of location and/or context when it is determined that the maintenance task is due within a threshold second period of time that is less than the first period of time. For example, if the first period of time is one week, the second period of time may be one day. In such a configuration, the device 60 can monitor for an optimal location and time to provide a reminder starting one week out from the deadline and up to one day before the deadline, after which the device 60 can automatically provide the maintenance reminder regardless of the location and context since failure to comply with the deadline poses potential health risks to the users. The second threshold period of time can be any of a variety of time periods (e.g., 6 hours, 12 hours, 1 day, 2 days, 1 week), and can vary depending on the type of maintenance activity to be performed and the maintenance model for the user.

In some cases, the system 400 determines a location where the user conducts a majority of maintenance activities and tracks the timing of diurnal pattern of maintenance activities at that location and determines one or more time periods when the user is likely to conduct maintenance activities and the device 60 provides the maintenance activity reminder during the diurnal period of time prior to the scheduled time for the maintenance activity if the user is at the location where the user conducts the majority of maintenance activities. In some cases, the maintenance reminder is held by the device 60 until the user arrives at the location where the user conducts a majority of maintenance activities if the user is not at that location during the diurnal period of time when the user conducts most maintenance activities. In some cases, the maintenance reminder is displayed by the device 60 at the time that the maintenance is scheduled regardless of whether the user is at the location where the user conducts a majority of maintenance activities. In some cases, the system 400 can recognize patterns regarding when a user leaves from and arrives at a location where they perform routine maintenance activities and schedule a reminder a predetermined time prior to when the user is expected to leave the location and/or holds reminders until the user arrives at the location if the user is expected to arrive at the location prior to when the time when the maintenance activity is scheduled.

Figure 5:
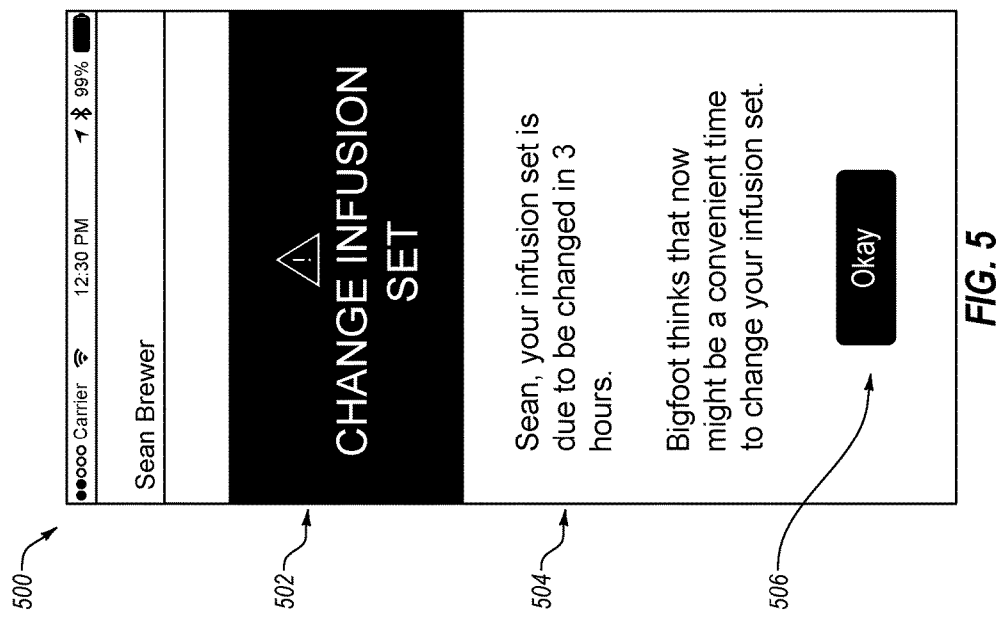
FIG. 5 is an example of a maintenance reminder in a user interface.

FIG. 5 depicts an exemplary maintenance reminder in a user interface 500. The maintenance reminder includes a banner message 502 briefly identifying the maintenance activity and indicating the severity of the deadline (e.g., via color, symbols, font size, font effects), a detailed message 504 describing what the user has to do to comply with the maintenance activity, and a confirmatory interface element 506 through which the user has to provide explicit input indicating that the user has viewed the notification in order for it to be dismissed.

Maintenance Activity User Interfaces

Figures 6C, 6D:
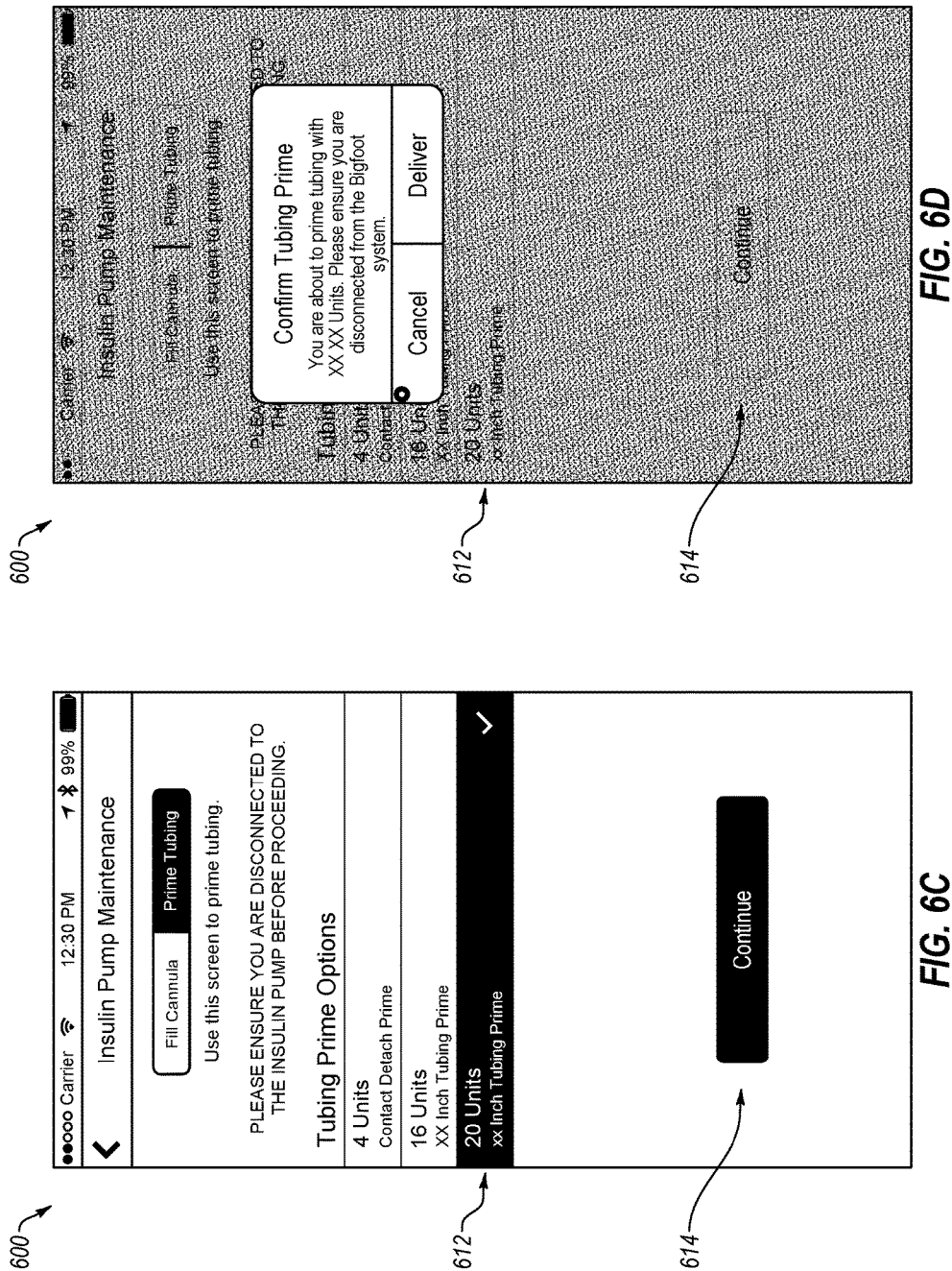

FIGS. 6A-6D depict an example pump maintenance user interface 600, which can be presented to the user when conducting pump maintenance. Referring to FIG. 6A, the interface 600 allows a user to select between conducting cannula fill operations 602 and tube priming operations 604. Once an option is selected, the user can press the continue button 606 to go to the next screen of the user interface 600, as depicted in FIG. 6B. In FIG. 6B, the user can confirm the selected cannula fill operation 608 by selecting the continue button 610, or can select the tubing prime tab 611. In response to selecting the tab 611, the user interface 600 allows the user to select from among tubing prime operations and to confirm the selected tubing prime operation 612 by selecting the continue button 614, as depicted in FIG. 6C. In response to selecting the continue 614 button, the user interface of FIG. 6D is presented to provide a warning 616 that the tubing is about to be primed. The warning 616 can include a confirmation text box over a shaded background, for example.

Providing Alarms to a Remote Server System Via Nearby Third Party Devices

Methods, devices, and systems provided herein can also trigger alarms regarding situations when a user needs to act quickly in order to keep the user safe. In some cases, however, a PWD may experience a condition where the user becomes non-responsive (e.g., a severe hypoglycemic event). Accordingly, to keep a PWD user safe, methods, device, and systems provided herein can send data, including location data, to a remote service for distribution people selected by the PWD, such as a family member or HCP, using a paired mobile computing device. For example, a PWD and parent may wish to have the parent review all CGM data and/or insulin delivery data, along with location data, in order for the parent to be comfortable that their child PWD is safe. In other cases, a PWD may wish to configure methods and systems provided herein so that their loved ones are only sent emergency alarms (e.g., blood glucose values greater than 400 mg/dl or below 55 mg/dl). A paired mobile computing device 60, however, can be left behind and/or run out of battery or otherwise lose the ability to connect with a pump assembly 15 and/or a CGM 50. Accordingly, in some cases, such as those discussed below, methods, devices, and systems provided herein can send data to a remote server for distribution to people selected by the PWD, HCPs, and/or emergency medicine providers though non-paired mobile computing devices under certain conditions.

Figure 7:
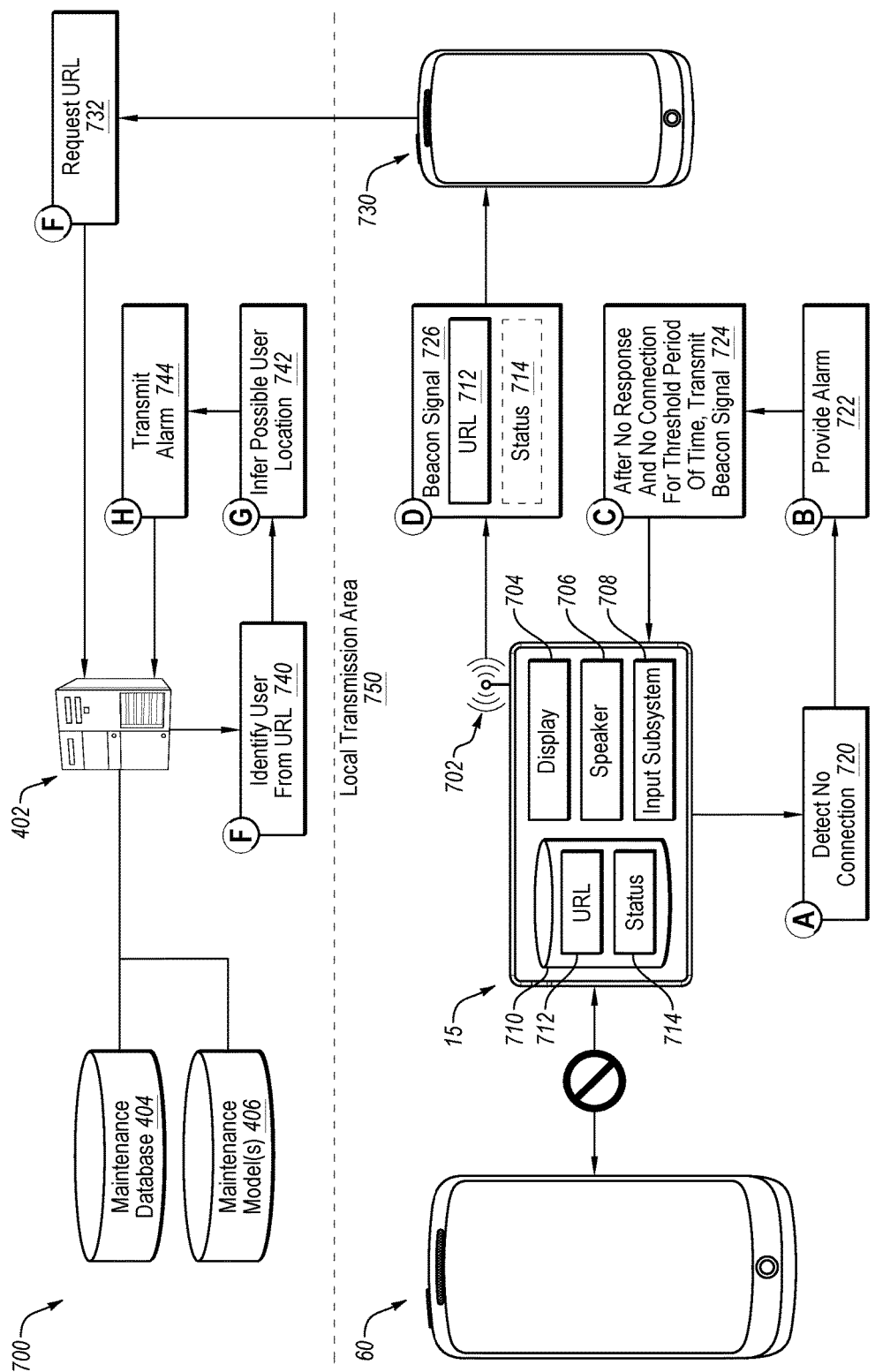
FIG. 7 depicts an example system and corresponding method for the insulin pump to transmit alerts back to the server system without its paired mobile device via nearby third party computing devices.

FIG. 7 depicts an example system 700 and corresponding method (steps A-H, 720-726 and 732-740) for the insulin pump 15 to transmit alarms back to the server system 402 without its paired mobile device 60 via nearby third party computing devices 730. Normally, without the mobile device 60, the insulin pump 15 may not otherwise be able to communicate with the outside world—meaning it would not be able to provide medical alerts back to the server system 402, which can be used to alert a user's doctor and/or emergency medical personnel, as needed if the insulin pump 15 detects an emergency situation.

The system 700 and the corresponding method (steps A-H, 720-726 and 732-740) can be used to provide a solution to these and other potential problems that may arise when the insulin pump 15 is left without a direct connection to the mobile device 60 and/or an indirect connection to the server system 402. In particular, the insulin pump 15 can transmit a local beacon signal (e.g., BLUETOOTH low energy (BLE) beacon signal, Wi-Fi beacon signal, near field communication (NFC) beacon) that other computing devices (e.g., mobile computing devices, non-mobile computing devices), such as the third party device 730, are programmed to listen for, detect, and use to request additional information. Such beacon signals can include a uniform resource locator (URL) that causes the result for additional information to be routed to the server system 402 along with a unique identifier for the mobile device 60, insulin pump 15, and/or user. The beacon signals can, in some cases, also include additional details related to the current status of the mobile device 60, the insulin pump 15, and/or the user, such as the last BG reading for the user, the most recent dosing information, the user's current medical condition, the last known location of the mobile device 60, and/or other relevant information that may be conveyed within a beacon signal having a limited number of bits. The third party device 730 can detect the beacon signal and automatically request the URL, which is designed to point to the server system 402 to alert the server system 402 of a potential medical danger/emergency with the user of the insulin pump 15.

Referring to step A (720), in response to detecting no connection with the mobile device 60, the insulin pump 15 can initial provide a local alert using an output subsystem on the pump 15 (step B, 722). The output subsystem of the insulin pump 15 can include, for example, a display 704 and a speaker 706 to visually and audibly alert the user as to the lost connection with the mobile device 60. The alert can include information identifying that the connection with the mobile device 60 has been lost and can advise the user to reconnect as soon as possible. The alert can also include a prompt for the user to provide input indicating that he/she has received and understood the alert. The user input can be provided via an input subsystem 708 on the insulin pump 15, which can include, for instance, one or more physical buttons, keypads, motion sensors, microphones, and/or other input mechanisms. If no response is received from the user within a threshold period of time of the alert being provided, then the insulin pump 15 can transition to transmitting beacon signals to nearby third party devices (step C, 724). For example, if the user is non-responsive or does not otherwise detect the alert, the lack of a connection with the mobile device 60 can pose a health risk for the user which can cause the automated escalation to transmitting beacon signals. Similarly, even if the user does acknowledge the alert with appropriate user input within the threshold period of time, but an alarm condition persists for a threshold period of time and is not acknowledged after a re-announcement of the alarm, then the insulin pump 15 may also begin transmitting beacon signals.

As indicated by step D (726), the insulin pump 15 can transmit a broadcast signal that includes a URL 712 for the server system 402 and optional status information 714. The URL 712 and status information 714 can be stored in a local storage system 710 (e.g., flash memory, non-volatile memory, volatile memory) on the insulin pump 15. The URL 712 can have embedded within it a unique identifier for the mobile device 60, the insulin pump 15, and/or the user. Such a unique identifier can be, for example, includes as a portion of the URL string or as a parameter included with the URL. The URL 712 can additionally include an encoding indicating that the transmission is a third-party alert based on the connection with the mobile device 60 being lost and not reestablished. Such an encoding can also be part of the URL string or a parameter in the URL. The beacon can optionally include the status information 714, which can indicate a recent status of the insulin pump 15, the mobile device 60, and/or the user, such as health information for the user (e.g., recent BG level), a health condition for the user, a recent location for the mobile device 60, and/or other relevant details. The status information can also be encoded as part of the URL string or as a parameter in the URL.

Any of a variety of appropriate wireless protocols and chipsets 702 can be used for the broadcast the beacon signal, such as standardized and widely adopted wireless protocols on mobile devices like BLE, Wi-Fi, and NFC. The local transmission area 750 (defining nearby devices that are able to receive and act upon the beacon signal) can depend on the chipset and wireless protocol that is used for the broadcast signal. For example, if the broadcast signal is transmitted using the Wi-Fi standard and chipset, the local transmission area 750 can be up to 30 m-40 m. For example, the insulin pump 15 can be programmed to use one or more wireless beacon protocols (e.g., APPLE's iBeacon, AltBeacon, URI-Beacon, GOOGLE Beacons) to transmit BLE beacon signals that include the URL 712 in the payload of the beacon message. Additionally, insulin pump 15 can be programmed to transmit the broadcast signal over multiple different wireless protocols (e.g., both Wi-Fi and BLE) to enhance the opportunity that the signal will be received by a nearby listener.

The third party device 730 can passively monitor for and detect beacon signals, such as the beacon signal 726, and to automatically request the URL 712 in response to detecting the signal 726. For example, the third party device 730 can be run with settings and/or a mobile app that is programmed to passively monitor for BLE beacon signals and, when detected, to request the URL 712 specified in the signal.

from the adventure management computer system 902. The BLE beacon signals can include one or more header fields and/or payload bits that both the guide computing device 904 and the participant computing devices 906, 908 are programmed to recognize as an adventure-related beacon signal, which can help filter beacon signals at the device level instead of having to reconcile the beacon signal with a remote system, such as the system 902 and/or a beacon platform that translates beacon identifiers into additional beacon-related data.

In response to detecting the signal, the third party device 730 can automatically request the URL (step E, 732), which causes the request to be routed to the server system 402. In response to receiving the request, the server system 402 can identify the user who is the subject of the alert from the URL based on the unique identifier included in the URL (step F, 740). The server system 402 can also attempt to infer a possible user location based on the request (step G, 742). For example, the server system 402 can examine any breadcrumbs that may point to the user's current whereabouts, including evaluating the maintenance database 404 for a most recent recorded location for the user and the maintenance model 406 to infer one or more likely locations for the user given the user's historical behavior patterns. Additionally, the server system 402 can attempt to infer the location of the user based on location information that may be provided with the request from the third party device 730, such as an IP address for the third party device 730 that can be correlated to a rough geographic location. In some cases, the status information 714 transmitted as part of the request may include at least a partial location indicator, such as a most recent location determined by the mobile device 60 (and shared with the insulin pump 15) and/or unique identifiers for nearby Wi-Fi base stations (e.g., MAC address for nearby Wi-Fi base station). Using as much information as possible about the user and his/her current location, at step H (744) the server system 402 can transmit alerts to people preapproved for the user (e.g., user's doctor, user's emergency contact) as well as to nearby emergency medical personnel, if warranted.

Figure 8:
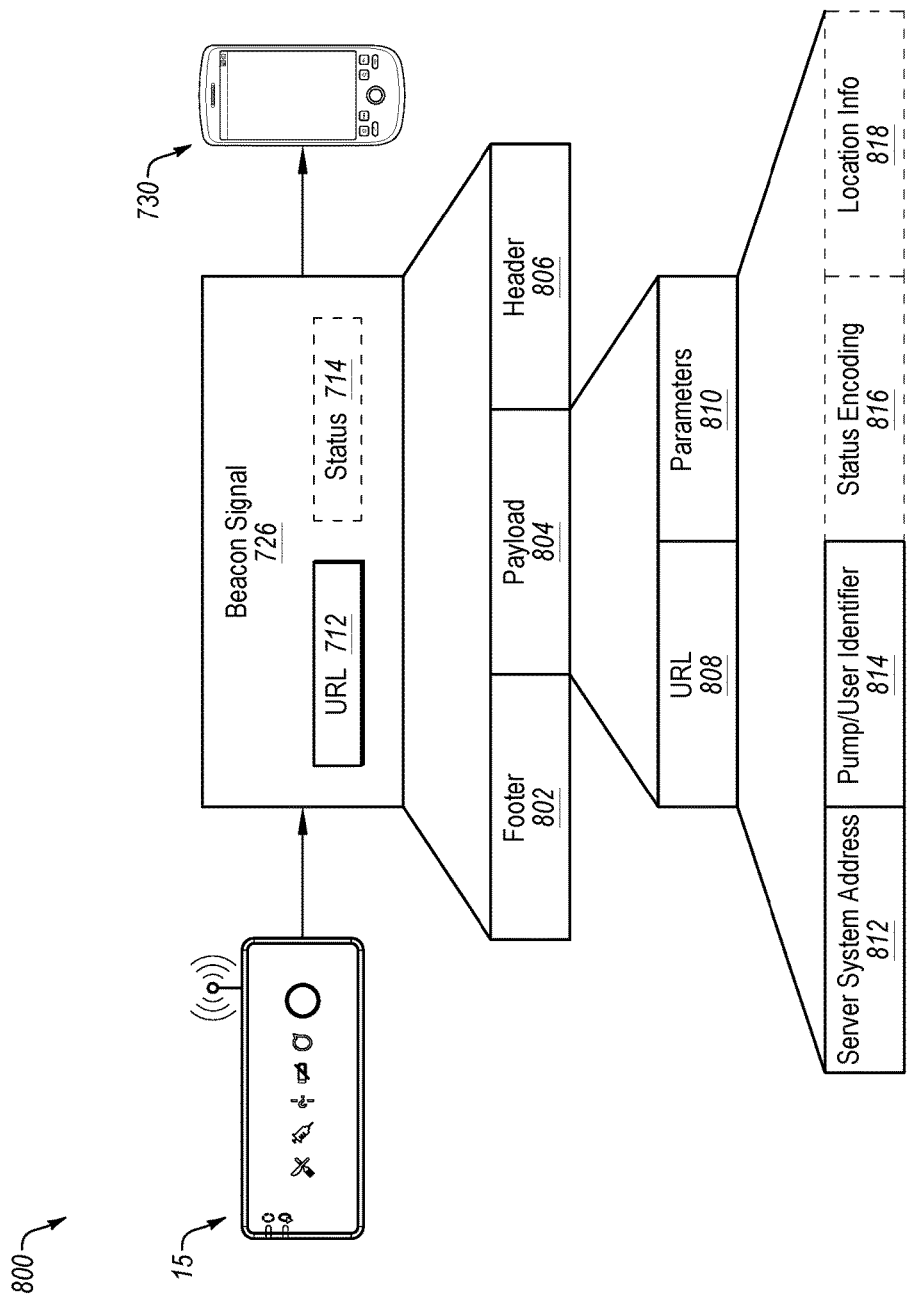
FIG. 8 is a conceptual diagram of an example system for local beacon signal transmissions.

FIG. 8 is a conceptual diagram of an example system 800 for local beacon signal transmissions. The system 800 includes the insulin pump 15 transmitting the beacon signal 726, which is detected by the third party device 730. The beacon signal 726 is transmitted as a data packet with a header 806, a payload 804, and a footer 802. The payload 804 includes the URL 808 for the server system 402 and parameters 810 appended to the end of the URL 808 with flags to indicate parameter names and values, and to differentiate between parameters. The URL 808 includes the server system address 812 (e.g., IP address, domain name, shortened URL for the server system 402), a unique identifier 814 for the pump/user, status encoding information 816, and any possible location information 818 available on the insulin pump 15. The server system address 812 can be included in the URL 808. The pump/user identifier 814, the status encoding 816, and the location info 818 can be included in either the URL 808 (e.g., part of the URL string) or in the parameters 810. How much of the status encoding 816 and the location info 818 that can be included in the packet can depend on the size of the information in bits. The beacon signal 726 can be limited to a certain number of bits, and the insulin pump 15 can be programmed to cap the information included in the packet at the bit limit for the packet.

Providing Alerts and Status Information on Nearby Mobile Computing Devices

Methods, devices, and systems provided herein can also allow for third-party mobile computing devices owned by PWD designated assistance entities (e.g., family members, friends, and/or caregivers) or otherwise authenticated to view data from one or more peripheral devices of a diabetes management system (e.g., data from an insulin pump) by direct wireless communication with the peripheral device. For example, if a PWD is traveling with a group of friends and/or family to a remote location without internet access using the system depicted in FIG. 1 having a primary user interface of the PWD's paired mobile computing device, the PWD may have concerns that the PWD won't be able to view system data if the PWD's paired mobile computing device becomes disabled, thus the PWD may decide to permit other mobile computing devices owned by friends and/or family to access data. In some cases, the PWD's paired mobile computing device can be adapted to issue commands to the insulin pump assembly, but the third party mobile computing devices can only be authorized to view data, which can mitigate against risks associated with multiple mobile computing devices being able to issue commands.

Figure 9:
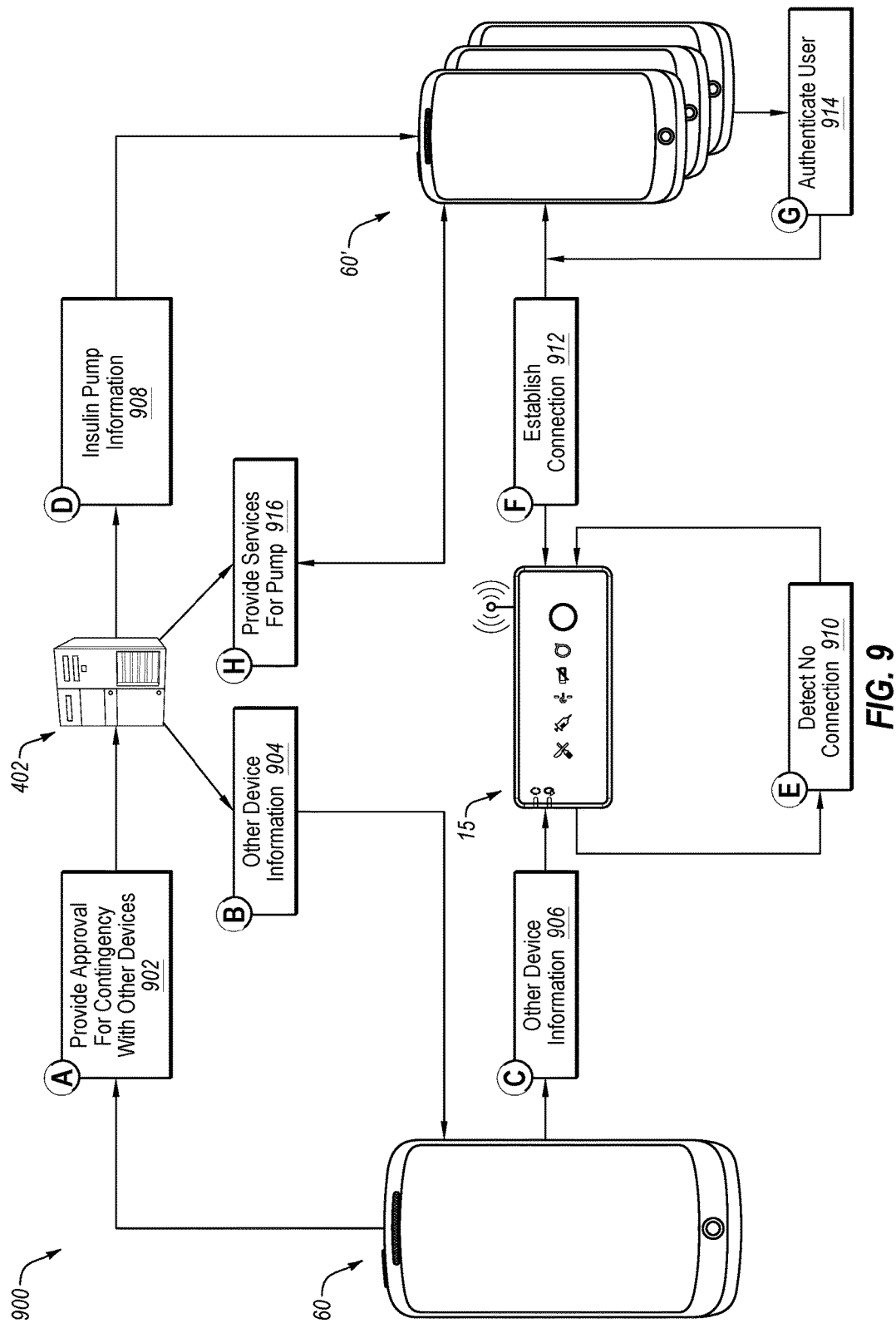
FIG. 9 depicts an example system and corresponding method for providing alerts and status information on nearby mobile computing devices.

FIG. 9 depicts an example system 900 and corresponding method (steps A-H, 902-914) for providing alerts and status information on nearby mobile computing devices. The system 900 and corresponding method solve similar problems to those addressed above in FIGS. 7-8, but do so by leveraging nearby mobile computing devices that are preapproved to display and possibly control operation of the insulin pump 15 in the event that the connection with the mobile device 60 is lost. As indicated by step A (902), the mobile device 60 can provide approval for contingency control of the insulin pump 15 by other devices 60' (e.g., other mobile computing devices registered with the server system 402 to control other insulin pumps for other users). The server system 402 can receive the approvals and provide information for the other devices 60' to the mobile device 60 (step B, 904), which can relay them to the insulin pump 15 (step C, 906). The information for the other devices 60' can include information that the insulin pump 15 can use to establish a secure and authenticated connection with the other devices 60' (and not unauthorized devices). Such information can include, for example, a MAC address for the other devices 60', a shared secret between the insulin pump 15 and the other devices 60', an authentication key and/or certificate for the other devices 60'. The insulin pump 15 can locally store this information for use in the event that the direct connection with the mobile device 60 and/or the indirect connection with the server system 402 (via the mobile device 60) is lost.

Similarly, the server system 402 can transmit information for the insulin pump 15 that the other devices 60' can use to establish a secure and authentic connection with the insulin pump 15. Such information can include, for example, a MAC address for the insulin pump 15, a shared secret between the other devices 60' and the insulin pump 15, and an authentication key and/or certificate for the insulin pump 15. The other computing devices 60' can store the information for use in the event that the insulin pump 15 attempts to establish a connection in the event that the direct connection with the mobile device 60 and/or the indirect connection with the server system 402 (via the mobile device 60) is lost.

In the depicted example, the connection with the mobile device 60 and/or the server system 402 is lost (step E, 910), which causes the insulin pump 15 to seek out any of the preapproved other devices 60' that are located nearby to establish a connection (step F, 912). In some cases, the insulin pump 15 does not establish a connection with the other devices 60', and instead simply broadcasts health-related information for the user that is passively monitored for by the other devices 60'. To ensure user privacy and safety, once a connection is established with one of the other devices 60' or once the other devices 60' detect the health-related information broadcast by the insulin pump 15, the user may need to authenticate himself/herself and/or otherwise provide consent for the other device 60' to display alerts, control, and/or operate the insulin pump 15 (step G, 914). The authentication can be performed between the other device 60' and the server system 402 (e.g., username/password verification, entering a PIN number, voice recognition, image recognition, fingerprint identification). Once authenticated, services for the insulin pump 15 and/or the health-related information for the user can be provided via the other device 60' and the server system 402 (step H, 916).

Continuous Glucose Monitor

Continuous glucose monitor 50 can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of characteristics of the user's blood (e.g., the user's blood glucose level or the like). In some cases, the sensor shaft 56 can measure glucose or another analyte in interstitial fluid or in another fluid and correlate that to blood glucose levels. In response to the measurements made by the sensor shaft 56, continuous glucose monitor 50 can employ the wireless communication device 54 to transmit data to a corresponding wireless communication device 247 housed in the pump system 15. In some cases, the monitoring device 50 may include a circuit that permits sensor signals (e.g., data from the sensor shaft 56) to be communicated to the communication device 54. The communication device 54 can transfer the collected data to the controller device 200 (e.g., by wireless communication to the communication device 247). Alternatively, the monitoring device 50 can employ other methods of obtaining information indicative of a user's blood characteristics and transferring that information to the controller device 200. For example, an alternative monitoring device may employ a micropore system in which a laser porator creates tiny holes in the uppermost layer of a user's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucose-sensing contact lenses. Invasive methods involving optical means of measuring glucose could also be added. In yet another example, the monitoring device can include an optical detection instrument that is inserted through the skin for measuring the user's glucose level. Furthermore, it should be understood that in some alternative implementations, the monitoring device 50 can be in communication with the controller device 200 or another computing device via a wired connection.

Blood Glucose Meter

DMS 10 may optionally communicate with blood glucose meter 70 in addition to (or as an alternative to) continuous glucose meter 50. For example, one or more test strips (e.g., blood test strips) can be inserted into a strip reader portion of blood glucose meter 70 and then receive blood to be tested. In some cases, blood glucose meter 70 is configured to analyze the characteristics of the user's blood and to communicate (e.g., via a Bluetooth wireless communication connection) the information to the controller device 200. In some cases, a user can manually input a glucose meter reading. Blood glucose meter 70 can be manually operated by a user and may include an output subsystem (e.g., display, speaker) that can provide the user with blood glucose readings that can be subsequently entered into the controller or user interface (to collect the data from an unconnected BGM into the system). Blood glucose meter 70 may be configured to communicate data (e.g., blood glucose readings) obtained to the controller device 200 and/or other devices, such as the mobile computing device 60. Such communication can be over a wired and/or wireless connection, and the data can be used by the controller device 200 and/or the mobile computing device 60 to perform multiple delivery modes and/or a secondary feedback loop for the insulin delivery system 10.

External Insulin Delivery Devices

DMS 10 may include one or more external medication delivery devices 80 (e.g., syringe, an insulin pen, a smart syringe with device communication capabilities, or the like) through which additional medicine dosages (e.g., insulin, glucagon) can be manually administered to a user. In some cases, user interfaces provided herein allow users to input a medication, a dosage amount, and the timing so that a closed-loop control algorithm can account for the additional medication. In some cases, mobile computing device 60 can make a recommendation for an amount of insulin to be delivered using an external delivery device.

Pump Assembly

Referring again to FIG. 1, pump assembly 15 can include pump device 100 configured to removably attach to the controller device 200 in a manner that provides a secure fitting, an overall compact size, and a reliable electrical connection. Additional details about the particularly depicted pump assembly 15 are described in more detail below in connection with FIGS. 1B and 1C.

Pump assembly 15 can be pocket-sized so that the pump device 100 and controller device 200 can be worn in the user's pocket or in another portion of the user's clothing. In some circumstances, the user may desire to wear the pump assembly 15 in a more discrete manner. Accordingly, the user can pass the tube 147 from the pocket, under the user's clothing, and to the infusion site where the adhesive patch can be positioned. As such, the pump assembly 15 can be used to deliver medicine to the tissues or vasculature of the user in a portable, concealable, and discrete manner.

In some cases, the pump assembly 15 can be configured to adhere to the user's skin directly at the location in which the skin is penetrated for medicine infusion. For example, a rear surface of the pump device 100 can include a skin adhesive patch so that the pump device 100 can be physically adhered to the skin of the user at a particular location. In these cases, the cap device 130 can have a configuration in which medicine passes directly from the cap device 130 into an infusion set 146 that is penetrated into the user's skin. In some examples, the user can temporarily detach the controller device 200 (while the pump device 100 remains adhered to the skin) so as to view and interact with the user interface 220.

Referring now to FIG. 1B, the pump device 100 in this example includes a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system (e.g., including a battery powered actuator, a gear system, a drive rod, and other items that are not shown in FIG. 5) that advances a plunger 125 in the fluid cartridge 120 so as to dispense fluid therefrom. In this example, the controller device 200 communicates with the pump device 100 to control the operation of the drive system. Optionally, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device (having a new fluid cartridge) to the reusable controller device 200 for the dispensation of fluid from a new fluid cartridge. Accordingly, the user is permitted to reuse the controller device 200 (which may include complex or valuable electronics, as well as a rechargeable battery) while disposing of the relatively low-cost pump device 100 after each use. Such a pump assembly 15 can provide enhanced user safety as a new pump device (and drive system therein) is employed with each new fluid cartridge. Additional and/or alternative implementations of the controller device 200 are also possible, including magnetic drive turbine (MDT) monolithic architecture pumps and/or omnipods.

The pump assembly 15 can be a medical infusion pump assembly that is configured to controllably dispense a medicine from the cartridge 120. As such, the fluid cartridge 120 can contain a medicine 126 to be infused into the tissue or vasculature of a targeted individual, such as a human or animal patient. For example, the pump device 100 can be adapted to receive a fluid cartridge 120 in the form of a carpule that is preloaded with insulin or another medicine for use in the treatment of Diabetes (e.g., Exenatide (BYETTA, BYDUREON) and liraglutide (VICTOZA)SYMLIN, or others). Such a cartridge 120 may be supplied, for example, by Eli Lilly and Co. of Indianapolis, Ind. Other examples of medicines that can be contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some cases, the pump device 100 can include one or more structures that interfere with the removal of the fluid cartridge 120 after the fluid cartridge 120 is inserted into the cavity 116. For example, the pump housing structure 110 can include one or more retainer wings (not shown) that at least partially extend into the cavity 116 to engage a portion of the fluid cartridge 120 when the fluid cartridge 120 is installed therein. Such a configuration may facilitate the "one-time-use" feature of the pump device 100. In some cases, the retainer wings can interfere with attempts to remove the fluid cartridge 120 from the pump device 100, thus ensuring that the pump device 100 will be discarded along with the fluid cartridge 120 after the fluid cartridge 120 is emptied, expired, or otherwise exhausted. In another example, the cap device 130 can be configured to irreversibly attach to the pump body 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, the pump device 100 can operate in a tamper-resistant and safe manner because the pump device 100 can be designed with a predetermined life expectancy (e.g., the "one-time-use" feature in which the pump device is discarded after the fluid cartridge 120 is emptied, expired, or otherwise exhausted).

Still referring to FIG. 1B, the controller device 200 can be removably attached to the pump device 100 so that the two components are mechanically mounted to one another in a fixed relationship. In some cases, such a mechanical mounting can also form an electrical connection between the removable controller device 200 and the pump device 100 (for example, at electrical connector 118 of the pump device 100). For example, the controller device 200 can be in electrical communication with a portion of the drive system (show shown) of the pump device 100. In some cases, the pump device 100 can include a drive system that causes controlled dispensation of the medicine or other fluid from the cartridge 120. In some cases, the drive system incrementally advances a piston rod (not shown) longitudinally into the cartridge 120 so that the fluid is forced out of an output end 122. A septum 121 at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device 130 to the housing structure 110. Thus, when the pump device 100 and the controller device 200 are mechanically attached and thereby electrically connected, the controller device 200 communicates electronic control signals via a hardwire-connection (e.g., electrical contacts along connector 118 or the like) to the drive system or other components of the pump device 100. In response to the electrical control signals from the controller device 200, the drive system of the pump device 100 causes medicine to incrementally dispense from the fluid cartridge 120. Power signals, such as signals from a battery (not shown) of the controller device 200 and from the power source (not shown) of the pump device 100, may also be passed between the controller device 200 and the pump device 100.

Cap device 130 of the pump device 100 can be configured to mate with an infusion set 146. In general, the infusion set 146 can be a tubing system that connects the pump assembly 15 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the user so that the medicine dispensed through the tube 147 passes through the cannula 149 and into the user's body. The cap device 130 can provide fluid communication between the output end 122 (FIG. 5) of the fluid cartridge 120 and the tube 147 of the infusion set 146.

Referring now to FIG. 1C, the controller device 200 (shown in an exploded view) houses a number of components that can be reused with a series of successive pump devices 100. In particular, the controller device 200 can include control circuitry 240 and a rechargeable battery pack 245, each arranged in the controller housing 210. The rechargeable battery pack 245 may provide electrical energy to components of the control circuitry 240, other components of the controller device (e.g., the display device 222 and other user interface components, sensors, or the like), or to components of the pump device 100. The control circuitry 240 may be configured to communicate control or power signals to the drive system of the pump device 100, or to receive power or feedback signals from the pump device 100.

The control circuitry 240 of the controller device 200 can include one or more microprocessors 241 configured to execute computer-readable instructions stored on one or more memory devices 242 so as to achieve any of the control operations described herein. At least one memory device 242 of the control circuitry may be configured to store a number of user-specific dosage parameters. Various user-specific dosage parameters can be automatically determined and/or updated by control operations implemented by the control circuitry 240 of the controller device 200. Additionally, the control circuitry 240 can cause the controller device 200 to periodically communicate the user-specific dosage parameters to the mobile computing device 60 for future use during operations by the mobile computing device 60 or for subsequent communication to cloud-based computer network.

In some cases, the control circuitry 240 can receive input data or other information from the mobile computing device 60 (e.g., via user input at the mobile computing device 60) and thereby cause the controller device 200 to output information to the mobile computing device 60 for display on the screen of the mobile computing device 60, such as settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the amount of battery life remaining, or the like). The control circuitry 240 can be programmable to cause the control circuitry 240 to change any one of a number of settings or modes of operation for the insulin delivery system 10. In some cases, the control circuitry 240 can include a cable connector (e.g., a USB connection port or another data cable port) that is accessible on an external portion of the controller housing 210. As such, a cable can be connected to the control circuitry 240 to upload or download data or program settings to the control circuitry.

A number of implementations have been described. Nevertheless, it will be understood that various modifications may be made without departing from the spirit and scope of the invention. Accordingly, other implementations are within the scope of the following claims.

What is claimed is:

1. A diabetes management system comprising:
one or more of a continuous glucose monitor and an insulin delivery device; and
a mobile controller device in wireless communication with the continuous glucose monitor, the insulin delivery device, or a combination thereof, the mobile controller device being adapted to (a) receive blood glucose levels for a user from the continuous glucose monitor or (b) receive insulin delivery data from the insulin delivery device, and wherein the insulin delivery device is adapted to output maintenance reminders to the user based, at least in part, on location information; the mobile controller device comprising:
a location subsystem to detect a location of the mobile controller device, the continuous glucose monitor, the insulin delivery device, or a combination thereof,
a maintenance model that models the user's behavior with regard to maintenance reminders based, at least in part, on locations and context for the diabetes management system when the maintenance reminders are presented to the user,
a maintenance subsystem (i) to continually update the maintenance model by (a) detecting or receiving indications that the user has conducted maintenance tasks on the diabetes management system and (b) updating the maintenance model based on the conducted maintenance tasks, and (ii) to continually provide maintenance reminders at optimal times for upcoming maintenance tasks by (a) obtaining a current location from the location subsystem, (b) determining a current context for the diabetes management system, and (c) identifying the optimal times and providing upcoming maintenance reminders for the upcoming maintenance tasks at the optimal times based on evaluation of the current context and the current location using the maintenance model.

2. The diabetes management system of claim 1, wherein the upcoming maintenance task is selected from the group consisting of recharging a continuous glucose monitor or an insulin delivery device, changing the sensor of a continuous glucose monitor, changing the infusion set of an insulin delivery device, changing the infusion location of an insulin delivery device, changing a sensor location for a continuous glucose monitor, refilling insulin into an insulin delivery device, changing an insulin containing cartridge in an insulin delivery device, replacing a battery in an insulin delivery device, or a combination thereof.

3. The diabetes management system of claim 1, wherein:
for a particular upcoming maintenance task, the maintenance subsystem begins monitoring for an optimal time to provide a particular maintenance reminder for the particular upcoming maintenance task upon a determination that the particular upcoming maintenance task is due within a threshold first period of time,
the monitoring includes repeatedly obtaining the current location, determining the current context, and identifying the optimal time to provide the particular maintenance reminder, and
the monitoring for the particular upcoming maintenance task is not performed before the particular upcoming maintenance task is due within the threshold first period of time.

4. The diabetes management system of claim 3, wherein the maintenance subsystem automatically provides the particular maintenance reminder regardless of the current location and the current context when the particular maintenance task is due within a threshold second period of time that is less than the first period of time.

5. The diabetes management system of claim 1, wherein:
the continually updating of the maintenance model includes the maintenance system (i) determining a particular location where the user conducts a majority of maintenance tasks, (ii) tracking the timing of a diurnal pattern of maintenance tasks at the particular location, and (iii) incorporating a diurnal period of time when the user is likely to conduct maintenance tasks representing the diurnal pattern of maintenance tasks into the maintenance model, and
the continually providing maintenance reminders includes providing the maintenance reminders during the diurnal period of time prior to the scheduled time for the maintenance tasks when the user is at the particular location where the user conducts the majority of the maintenance tasks.

6. The diabetes management system of claim 5, wherein the maintenance reminders are held until the user arrives at the particular location where the user conducts the majority of maintenance tasks when the user is not at the particular location during the diurnal period of time when the user conducts most maintenance tasks.

7. The diabetes management system of claim 6, wherein the maintenance reminders are displayed at particular times when the maintenance tasks are scheduled regardless of whether the user is at the particular location where the user conducts a majority of maintenance tasks.

8. A wearable insulin delivery device comprising:
an insulin pump device to administer insulin dosages to a patient wearing the insulin delivery device;
one or more sensor interfaces to obtain, at least, blood glucose levels for the patient;
a wireless interface to wirelessly communicate with one or more other computing devices;
a data storage device to store a uniform resource locator (URL) for a remote server system and a unique identifier for the patient;
an input subsystem to receive input from the patient;
an output subsystem to output information to the patient; and
a controller (i) to control the insulin pump device delivering insulin to the patient based, at least in part, on the blood glucose levels received through the one or more sensor interfaces, (ii) to securely communicate with a paired mobile computing device that is authorized to communicate with the remote server system regarding the patient, (iii) to automatically output an alarm via the output subsystem in response to an alarm condition, and (iv) to transmit a wireless beacon signal using the wireless interface in response to the patient failing to provide a response via the input subsystem within a threshold period of time of the alert being output, wherein the beacon signal (i) includes, at least, the URL encoded with the unique identifier for the patient and (ii) is configured to prompt a third party computing device passively monitoring for beacon signals to transmit a request to the remote server system using the encoded URL.

9. A diabetes management system comprising:

a paired mobile computing device that is registered with a remote server system in association with a patient;

one or more other computing devices that are registered with the remote server system in association with one or more other patients, wherein the one or more other computing devices are (i) preauthorized by the patient to receive and present health-related information from the patient, and (ii) to passively monitor for the health-related information transmitted over one or more local wireless protocols; and a insulin delivery device comprising:
 an insulin pump device to administer insulin dosages to the patient;
 one or more sensor interfaces to obtain, at least, blood glucose levels for the patient;
 a wireless interface to wirelessly communicate with the paired mobile computing device and the one or more other computing devices;
 a data storage device to store (i) a unique identifier for the patient, (ii) authentication information to pair and securely communicate with the paired mobile computing device, and (iii) encryption information to securely broadcast the health-related information to the one or more other computing devices; and
 a controller (i) to control the insulin pump device delivering insulin to the patient based, at least in part, on the blood glucose levels received through the one or more sensor interfaces, (ii) to securely communicate with the paired mobile computing device, and (iii) to broadcast secure wireless signals including the health-related information for detection and presentation to the one or more other computing devices in response to detecting no connectivity with the paired mobile computing device.

10. The insulin delivery device of claim 8, wherein the third party computing device is configured to receive the wireless beacon signal when located within a wireless beacon signal range of the controller.

11. The diabetes management system of claim 9, wherein the one or more other computing devices are configured to receive secure wireless signals when located within a wireless signal range of the controller.

* * * * *